(12) United States Patent
Yoshikawa et al.

(10) Patent No.: US 11,955,207 B2
(45) Date of Patent: Apr. 9, 2024

(54) LABORATORY EXPERIMENT DATA EXPLORATION AND VISUALIZATION

(71) Applicant: Emerald Cloud Lab, Inc., South San Francisco, CA (US)

(72) Inventors: Alex M. Yoshikawa, South San Francisco, CA (US); Anand V. Sastry, South San Francisco, CA (US); Asuka Ota, South San Francisco, CA (US); Ben C. Kline, South San Francisco, CA (US); Bradley M. Bond, South San Francisco, CA (US); Brian M. Frezza, Redwood City, CA (US); Cameron R. Lamoureux, South San Francisco, CA (US); Catherine L. Hofler, South San Francisco, CA (US); Cheri Y. Li, South San Francisco, CA (US); Courtney E. Webster, South San Francisco, CA (US); Daniel J. Kleinbaum, Redwood City, CA (US); George N. Stanley, South San Francisco, CA (US); George W. Fraser, Mountain View, CA (US); Guillaume Robichaud, South San Francisco, CA (US); Hayley E. Buchman, South San Francisco, CA (US); James R. McKernan, South San Francisco, CA (US); Jonathan K. Leung, Sunnyvale, CA (US); Paul R. Zurek, South San Francisco, CA (US); Robert M. Teed, South San Francisco, CA (US); Ruben E. Valas, South San Francisco, CA (US); Sean M. Fitzgerald, South San Francisco, CA (US); Sergio I. Villarreal, South San Francisco, CA (US); Shayna L. Hilburg, South San Francisco, CA (US); Shivani S. Baisiwala, South San Francisco, CA (US); Srikant Vaithilingam, South San Francisco, CA (US); Wyatt J. Woodson, South San Francisco, CA (US); Yang Choo, South San Francisco, CA (US); Yidan Y. Cong, South San Francisco, CA (US)

(73) Assignee: Emerald Cloud Lab, Inc., South San Francisco, CA (US)

( * ) Notice: Subject to any disclaimer, the term of this patent is extended or adjusted under 35 U.S.C. 154(b) by 1151 days.

(21) Appl. No.: 15/740,581

(22) PCT Filed: Jun. 30, 2016

(86) PCT No.: PCT/US2016/040589
§ 371 (c)(1),
(2) Date: Dec. 28, 2017

(87) PCT Pub. No.: WO2017/004469
PCT Pub. Date: Jan. 5, 2017

(65) Prior Publication Data
US 2018/0190386 A1 Jul. 5, 2018

Related U.S. Application Data

(60) Provisional application No. 62/186,928, filed on Jun. 30, 2015, provisional application No. 62/186,936, filed on Jun. 30, 2015.

(51) Int. Cl.
*G16B 5/00* (2019.01)
*G06Q 10/00* (2023.01)
(Continued)

(52) U.S. Cl.
CPC ............... *G16B 5/00* (2019.02); *G06Q 10/00* (2013.01); *G16B 45/00* (2019.02); *G16B 50/00* (2019.02);
(Continued)

(58) Field of Classification Search
None
See application file for complete search history.

(56) References Cited

U.S. PATENT DOCUMENTS 6,813,473 B1  11/2004 Bruker
7,761,281 B2   7/2010 Bankes
(Continued)

FOREIGN PATENT DOCUMENTS

JP  2001215230  8/2001
JP  2005106746  4/2005
(Continued)

OTHER PUBLICATIONS

European Search Report and Opinion dated Feb. 18, 2019 for EP Application No. 16818856.3. 16 pages.
(Continued)

*Primary Examiner* — G. Steven Vanni
*Assistant Examiner* — Robert James Kallal
(74) *Attorney, Agent, or Firm* — Sheppard Mullin Richter & Hampton LLP

(57) ABSTRACT

The disclosure provides systems and methods for data analysis of experimental data. The analysis can include reference data that are not directly generated from the present experiment, which reference data may be values of the experimental parameters that were either provided by a user, computed by the system with input from a user, or computed by the system without using any input from a user. Another example of such reference data may be information about the instrument, such as the calibration method of the instrument.

7 Claims, 29 Drawing Sheets

(51) Int. Cl.
- G16B 45/00 (2019.01)
- G16B 50/00 (2019.01)
- G16B 50/30 (2019.01)
- G16C 20/80 (2019.01)
- G16C 20/90 (2019.01)
- G16H 10/40 (2018.01)
- G16H 40/40 (2018.01)
- G16H 40/60 (2018.01)
- G16H 50/50 (2018.01)

(52) U.S. Cl.
CPC ............ *G16B 50/30* (2019.02); *G16C 20/80* (2019.02); *G16C 20/90* (2019.02); *G16H 10/40* (2018.01); *G16H 40/40* (2018.01); *G16H 40/60* (2018.01); *G16H 50/50* (2018.01); *Y02A 90/10* (2018.01)

(56) References Cited

U.S. PATENT DOCUMENTS

| | | |
|---|---|---|
| 2002/0144905 A1 | 10/2002 | Schmidt |
| 2005/0089900 A1 | 4/2005 | Fujisaki et al. |
| 2006/0019333 A1 | 1/2006 | Rodgers et al. |
| 2006/0148063 A1 | 7/2006 | Fauzzi et al. |
| 2006/0241868 A1 | 10/2006 | Sun et al. |
| 2007/0143240 A1 | 6/2007 | Goldwasser et al. |
| 2007/0162411 A1 | 7/2007 | Kupershmidt et al. |
| 2008/0263468 A1* | 10/2008 | Cappione ............ G06F 3/04817 702/19 |
| 2008/0301202 A1* | 12/2008 | Boyce ................ G06K 9/00127 |
| 2013/0080373 A1 | 3/2013 | Yeck et al. |
| 2014/0229418 A1 | 8/2014 | Graham, II et al. |

FOREIGN PATENT DOCUMENTS

| | | |
|---|---|---|
| JP | 2009216705 | 9/2009 |
| JP | 2011153960 | 8/2011 |
| WO | WO2002068963 | 9/2002 |
| WO | WO 2010/086862 | 8/2010 |
| WO | WO 2017/004469 | 1/2017 |
| WO | WO-2017004468 | 1/2017 |
| WO | WO-2019066238 A2 | 4/2019 |
| WO | WO-2019066238 A3 | 6/2019 |

OTHER PUBLICATIONS

International Search Report and Written Opinion dated Nov. 16, 2016 for PCT/US2016/040589. 9 pages.
Proffiff. Robots for Hire: Emerald Launches Robotic Laboratories for Life Sciences. Bio-IT World. Jul. 1, 2014. 2 pages.
Rawat. Emerald Cloud Lab: Taking Biotech to the Cloud. SynBioBeta. Jul. 25, 2014. 2 pages.
Tanenbaum. Emerald Cloud Takes the Development of New Medications on Line. Jewish Business News. Jul. 11, 2014. 2 pages.
Webb. Democratizing biotech research. O'Reilly Radar. Feb. 5, 2015. 4 pages.
Wolfram. A Mathematica-Based Research Workflow at Work. Youtube.com. Dec. 17, 2012. 1 page.
Wolfram. The Emerald Cloud Lab: Data Lessons Learned from Running a Remote-Controlled Lifesciences Laboratory. Youtube.com. Oct. 8, 2014. 2 pages.

* cited by examiner

Notebook: *HIV Expression.nb* — 103

In[1]:= compile[
 experiment[WesternBlot],
 {ID[Sample,Protein,2331],
  ID[Sample,Protein,2332],
  ID[Sample,Protein,2334]},
 ID[Sample,Antibody,56],
 SampleVolume -> 5 Micro Liters,
 SeparationTime -> 27 Minutes,
 SeparationVoltage -> 375 Volts

501

Projects / Samples / Models / Reports / Data

Commands
- Plot Data
- Analyze Data
- Search Data
- Share Data
- Publish Data
- Compile Experiment
- Run Simulation
- Ship Materials

Experiments
- Thermodynamics
- Genomic DNA Prep
- Transfection
- UV/Vis Kinetics
- UV/Vis Spectroscopy
- UV/Vis Thermodynamics
- Vacuum Filtration
- Viral Prep
- Volume Check
- Western Blot

Protein Samples
- ID[Sample,Protein,2331]
- ID[Sample,Protein,2332]
- ID[Sample,Protein,2334]

Antibody Samples
- ID[Sample,Antibody,56]

Variables

| | | | |
|---|---|---|---|
| Replicates | 1 | Primary Washes | 2 |
| Literature | 5 | Primary Wash Volume | 150 (μL) |
| Sample Volume | 10 (μL) ▼ ul | Primary Wash Time | 30 (m) |
| Antibody Volume | 5 (μL) | Secondary Washes | 1 |
| Luminol Volume | 150 (μL) | Secondary Wash Volume | 150 (μL) |
| Peroxide Volume | 150 (μL) | Secondary Wash Time | 30 (m) |
| HRP Volume | 10 (μL) | Separation Time | 25 (m) |
| | | Separation Voltage | 350 (V) |
| | | Stacking Time | 3 (m) |
| | | Stacking Voltage | 200 (V) |
| | | Exposure Time | 100 (s) |
| | | Number of Blockings | 1 |
| | | Block Volume | 200 (μL) |
| | | Block Time | 5 (m) |

[Execute Experiment]

Notebook: *HIV Expression.nb* — 103

In[1]:= compile[
 experiment[WesternBlot],
 {ID[Sample,Protein,2331],
 ID[Sample,Protein,2332],
 ID[Sample,Protein,2334]},
 ID[Sample,Antibody,56],
 SampleVolume -> 5 Micro Liters,
 SeparationTime -> 27 Minutes,
 SeparationVoltage -> 375 Volts
 ]

Out[1]= ID[Experiment,WesternBlot,1314]

Success!

Your Western Blot Experiment was Sent to the Emerald Cloud Lab.

Projects | Samples | Models | Reports | Data

FIG. 7

LABORATORY EXPERIMENT DATA EXPLORATION AND VISUALIZATION

CROSS-REFERENCE TO RELATED APPLICATIONS

This application is a U.S. National Stage Application under 35 U.S.C. § 371 of International Application No. PCT/US2016/040588, filed Jun. 30, 2016, which application claims the benefit under 35 U.S.C. § 119(e) to U.S. Provisional Application Ser. Nos. 62/186,928 and 62/186,936, both filed on Jun. 30, 2015, the content of each of which is hereby incorporated by reference in its entirety.

BACKGROUND

Data visualization and analysis are important tools in life science researches. Data visualization is the application of computer graphics, scientific visualization, and information visualization to interpreting and exploring experimental data. Examples include visualization of HPLC curves, gel electrophoresis images, DNA and protein sequences, genomes, alignments, phylogenies, macromolecular structures, systems biology, microscopy, and magnetic resonance imaging data. Software tools available to assist with data visualization and analysis typically require importation of data from a different source and lack the ability to integrate such data to additional information that is useful for the visualization and analysis.

A life sciences research project typically involves a large number of steps over an extended period of time, and each step may require a different instrument and have different input and output samples. For instance, a screening for siRNA can involve siRNA synthesis, purification, verification and quantification, cell-free assay, and in vitro testing. No single instrument has been designed to carry out such a great variety of experiments, and there is currently no system or method for flexibly specifying and automating such multi-technique, multi-instrument, multi-platform research projects. Indeed, many in the art regard a generalized experimentation platform as impossible due to the potential for nearly exponentially many combinations of techniques and the myriad of specific parameters that can be varied within each technique. Despite ambitious claims of flexibility by some, the practical reality within the field is that functioning systems focus on automating or electronically representing a small, restricted, well-defined set of experiments centered around a specific task, e.g., high throughput screening of ligands for a specific enzyme. This restricted approach "addresses" the exponential scale of the generalization problem by avoiding it entirely, and therefore does not provide the technological foundation for building a truly flexible general experimentation system as disclosed herein.

One reason for this is that existing electronic systems for managing, storing, and viewing experimental data do not specify the experimental protocols used in a machine-readable form amenable to computerized analysis and reasoning. Thus, even when a computer has access to raw experimental data, it lacks a rich understanding of the experimentation that generated the raw data. For example in the Indigo Electronic Lab Notebook ("ELN"), the experimental protocol is just free text. See, e.g., EPAM Life Sciences, *Indigo ELN User Guide Version* 1.2, FIG. 18, bottom right panel. Thus, information regarding the experimental setup in the Indigo ELN is not machine parsable and one cannot programmatically validate or relate the experimental protocol information embodied by the free text to other information stored in the system. One consequence of this, as is observed in many fields, is that it is not possible to verify the completeness of the experimental protocol information contained in the free text. Another consequence of this is the inability to link experimental protocol information and resulting experimental data together, making it impossible to implement an efficient, reliable, and scalable general framework for linking experiments together.

SUMMARY

The disclosure provides, in some embodiments, systems and methods for data analysis of experimental data. The analysis can include reference data that are not directly generated from the present experiment, which reference data may be values of the experimental parameters that were either provided by a user, computed by the system with input from a user, or computed by the system without using any input from a user. Another example of such reference data may be information about the instrument, such as the calibration method of the instrument.

In one embodiment, a system is provided for analyzing data obtained from a laboratory experiment, comprising a processor, memory, and program code that comprises an experiment module configured to store values for experimental parameters for executing an experiment; a data module configured to store results from the experiment; an instrument module configured to store information about the instrument on which the experiment was run; an environment module configured to store environmental conditions under which the experiment was run; and a data visualization module configured to display a visual representation of the results stored in the data module, wherein the visual representation further comprises representation of one or more reference data point selected from the group consisting of the values for the experimental parameters, the information about the instrument and the environmental conditions.

Another embodiment provides a system for analyzing data obtained from a laboratory experiment, comprising a processor, memory, and program code comprising an experiment module configured to display identification of a sample used in an experiment, identification of an instrument for carrying out the experiment, identification of a data set generated from the experiment, and identification of an environmental record that comprises measurement of environmental conditions when and where the experiment was conducted, a data module configured to display data extract or visualization to represent a data set, identification of an experiment that generated the data set, and identification of an analysis performed on the data set; an instrument module configured to display a listing of experiments carried out on an instrument, a listing of control experiments run on the instrument, and a maintenance record for the instrument; an analysis module configured to display identification of a data set for which an analysis was made, and an analysis summary or figure that represents a result of the analysis; and an environment module configured to display environmental conditions when and where an experiment was conducted, wherein the system enables a user to explore information pertaining to an experiment while the user is presented with an experiment panel displayed by the experiment module, by: (1) allowing the user to click on the identification of a data set generated from the experiment on the experiment panel, and thereby invoking the data module to display identification of an analysis performed on the data set on a data panel, which allows the user to click on the identification of analysis performed on the data set to invoke the analysis module to display an analysis summary or figure that represents a result of the analysis on an analysis panel; (2) allowing the user to click on the identification of an environmental record and thereby invoking the environment module to display environmental conditions when and where the experiment was conducted; and (3) allowing the user to click on the identification of an instrument for carrying out the experiment and thereby invoking the instrument module to display, on an instrument panel, a listing of control experiments run on the instrument, and a maintenance record for the instrument relevant to the experiment.

The present disclosure, in some embodiments, also provides systems, methods, computer-readable media, modules, and means for implementing an integrated system for laboratory experiment design, adjustment, scheduling, compiling, execution, analysis, visualization, validation, and sharing. Such a system is able to accommodate heterogeneous samples to be run on heterogeneous instruments for heterogeneous experiment types. Moreover, the different samples, experiments and instruments are integrated such that the information from different entities can be shared to benefit the design, validation, and analysis of experiments.

The integration of the system of some of the embodiments of the present disclosure can be advantageous in at least a few aspects. For example, after a user enters one or more parameters for an experiment, the system can validate the parameters, suggest alternative or optimal parameters, adjust other parameters accordingly, or fill in other parameters for which no input is given by the user. Therefore, without limited input from the user, the system can generate a complete set of instructions and parameters for executing an experiment leading to high predictability and reproducibility. Such instructions can be itemized, linearized, parallelized, other otherwise optimized, and which provide unambiguous commands for carrying out an experiment.

Another advantage is that the integrated system allows a user to perform analysis in the same interface that specifies the experiments which generates data, receives the generated data, and/or facilitates the design of additional experiments after the data is generated. Even though not always visible, the present system in certain embodiments generates a complete set of specified parameters for an experiment.

The disclosed invention is differs from conventional technology, which employs free unstructured entry for information that is difficult to categorize or quantitate. In one embodiment the present technology provides support for a programming language inside the user interface supporting structured input of both desired actions, e.g., experiments, and data. Compared to the plethora of free text entry systems available in the art, the use of a programming language allows one to relate together specification of experiment, the actual execution of the experiment, the data generated, and analysis that data in one linear progression in one environment. Further, the elements of that progression as well as the overall progression are machine readable and amenable to unambiguous computational processing.

In accordance with one embodiment of the present technology, the systems makes guarantees at each step during design of an experiment, which is not practically possible in a fragmented system. A guarantee in this context means that description of an experiment protocol is complete, i.e., all information needed to perform the experiment is included. In another aspect, the guarantee is that that the experiment protocol is automatically linked to logs detailing actual experiment run, control logs, samples outputted, and data generated. In some embodiments, links are used to relate one experiment protocol to another. Instead of simply copying and pasting the original experimental protocol and then altering the input sample, a user can directly reference the original experiment and then specify only what the user wants to be done differently, e.g., different sample input, different temperature, without limitation. This advantageously allows for very compact and easy to read code without any loss of completeness, precision, or reproducibility. In accordance with one embodiment of the present technology, the systems is configured to guarantee that when a user copies an experimental protocol, rerunning with new parameters or inputs can be accordingly adjusted and validated.

Another embodiment of the present disclosure relates to programmatically offering sensible default settings for an experiment. The user only needs to specify that which is different. This is not possible if the experiment is not represented in a machine computable form, e.g., free text. Also, the default settings greatly improve ease of use by not forcing user to enter every single parameter an experiment requires. Yet in another embodiment, the experiment is automatically linked to logistical information about materials used in experiment, e.g., age of stock solution used.

Another advantage of certain embodiments of the technology is that the analysis module can automatically understand output of the experiment, because in specifying experiment up front the system is contextually aware of definition of the output.

BRIEF DESCRIPTION OF THE DRAWINGS

The figures of the accompanying drawings describe provided embodiments by way of illustration only, in which:

FIG. 5 shows a user interface that allows the user to adjust experimental parameters;

FIG. 6A shows that certain experimental parameters have been adjusted by the user;

FIG. 6B shows that, upon evaluating the entered value for the parameter, a warning is given by the system;

FIG. 7 shows that the system confirms that a valid experiment has been successfully designed by the user and accepted by the system;

Figure 1:
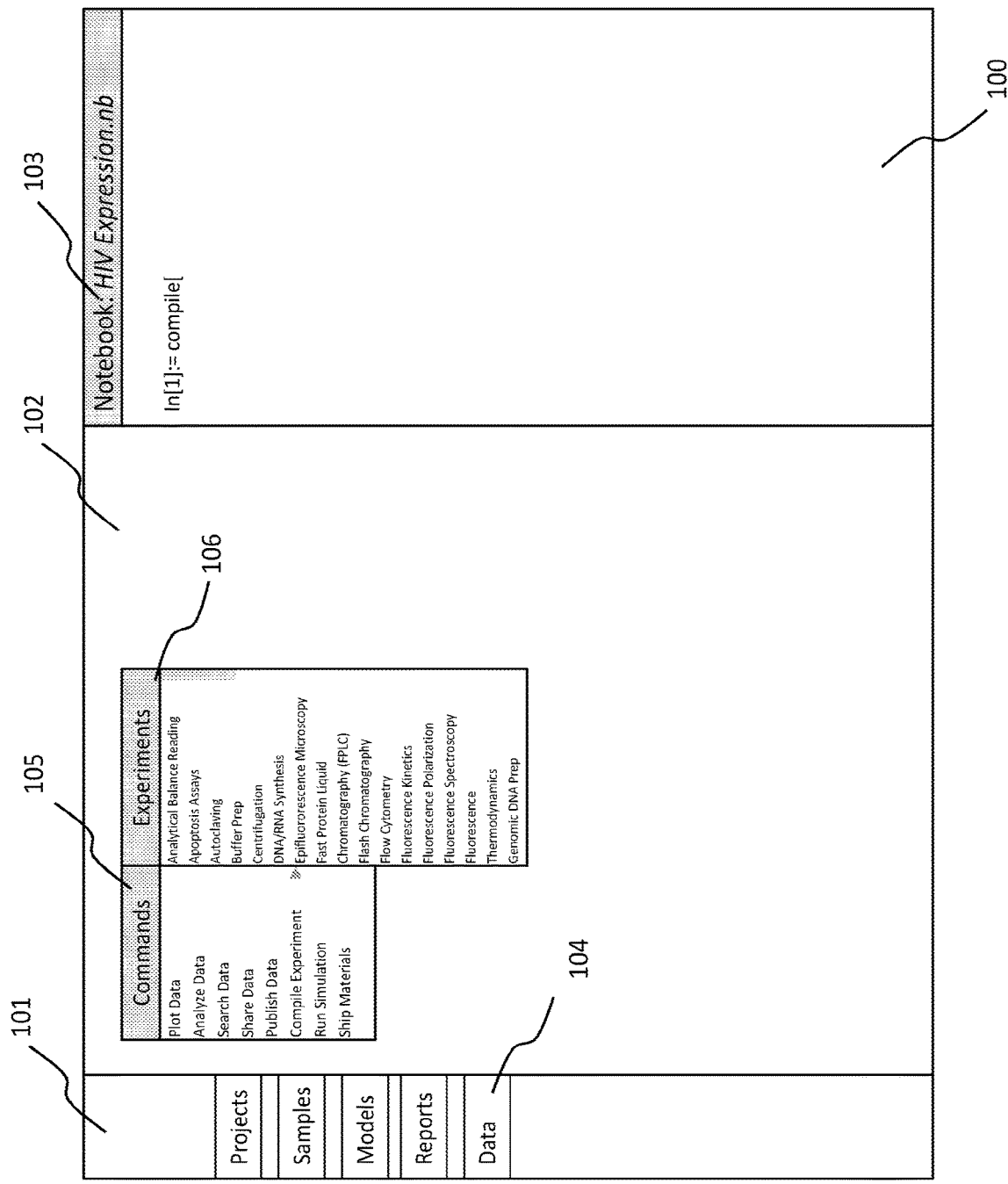
FIG. 1 shows a user interface for selecting an experiment type to be run on a system of the present disclosure.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow.

DETAILED DESCRIPTION

This disclosure provides systems and methods for conducting and managing integrated laboratory experiments. The system can include a variety of laboratory instruments that are connected to or interconnected with one or more computers. The computer can be local or remote relative to the individual instruments it controls, send commands to each individual instrument, and receive output. The computer can operate individually or as part of a larger group of computers, e.g., a datacenter. To facilitate communication between user, instruments, and computers, a computer language package, referred to as "Symbolic Lab Language" (SLL) based on the Mathematica® language from Wolfram Research (Champaign, IL), has been developed. SLL script and syntax are presented for the purpose of illustrating conceptual aspects of one or more embodiments with the explicit understanding that they will not be used to limit the scope or the meaning of the claims that follow. Further, a user interface (e.g., graphical user interface, web interface, Windows or Mac interface or mobile interface) can be created that enables users who are not familiar with the computer language to use the system efficiently.

User Interface for Experimental Design and Management

FIGS. 1-7 illustrate a computer user interface for a user to design a laboratory experiment (or simply an "experiment") to be run by one embodiment of the system of the present disclosure. The term "experiment" as used herein refers to a procedure undertaken to make a discovery, test a hypothesis, or demonstrate a fact that involves the use of a biological or chemical sample or reagent. It is appreciated that an experiment can be as simple as a single step and does not require a biological or chemical reaction (e.g., checking the absorbance at 260 nm for a sample). It is also to be understood that an experiment does not need to be as complete as needed to make a conclusory finding or approving or disapproving a hypothesis. The term "technique" as used herein refers to specialized procedures and methods used to carry out a particular task, especially the execution or performance of a scientific procedure. To improve clarity in this disclosure, the term technique shall be used to refer to individual steps that can be combined to perform an experiment. However, this is purely for clarity and does not limit the scope and definition of the term experiment as used in this disclosure, e.g., a technique is also an experiment. Finally, as used herein the term "protocol" refers to a plan for a scientific experiment. As with technique, this term is used for clarity of prose and is not intended to limit the definition or scope of the term experiment, e.g., the term experiment in context can refer to the protocol for that experiment.

In FIG. 1, the interface 100 includes a menu area 101, a main panel 102 and a computer script panel 103, sometimes referred to herein as a "notebook," "lab notebook," or "electronic lab notebook." The term "script" as used herein refers to instructions written in a computer programming or scripting language that may be executed with or without previous compilation into a machine language program. The computer script panel is configured to interactively display and process instructions written in a programming or scripting language, and may optionally also be configured to display and process plain text, data, images, and other media. Panels may also be embedded within other panels. For example, in some embodiments the script panel is configured to include data, experiment, visualization, and other panels as disclosed herein. These panels may be invoked via the graphical user interface or as a result of script commands entered in the script panel. Similarly, modules, as discussed elsewhere in this disclosure, may also be embedded within other panels and modules. The menu area includes a list of menu options 104 for a user to choose from, at any point during the use of the interface. Menu item "Projects" allows a user to organize experiments, including in the form of experiments recorded in notebooks, and create, view, modify, delete, share, or experiment projects. "Samples" allows a user to add, modify, annotate, select, delete, or check samples. As samples can be provided by a user from a remote location, the Samples menu also allows the user to check receiving status, amount and condition of the samples, etc. Menu item "Models" gives a user access to a variety of conceptual frameworks, ontological entities, controlled terminology, controlled taxonomies, or other knowledge representation schema that parameterize, among other things, the physical properties that may be associated with samples, as well conceptual placeholders for physical objects. "Reports" displays the reports generated by the system during or following an experiment, allows a user to generate visualization, extract, or manipulate data, and inspect experimental process and conditions. Without limitation, yet another menu item "Data" provides access to raw, processed, organized, or extracted data. The menu options that can be presented in the menu area or otherwise available for use are not limited to those exemplified above or illustrated in FIG. 1. For example, additional menu options can include "Experiment," "Plot," "Simulation," "Analysis," and "Search," without limitation.

When creating a new project, the main panel 102 will display relevant information to a user and allow the user to enter suitable input. For instance, as shown in FIG. 1, from a plurality of commands (105), the user selects "Compile Experiment" and, in response, the interface shows a listing of available experiment types in 106. Compiling an experiment refers to the process of authoring or validating the script defining that experiment, including validating specified parameters (including samples), deriving values for unspecified parameters, generating computer objects needed to execute the script, and optionally carrying out the experiment in the laboratory, delivering a result and/or analyzing the result. In some embodiments the term "execute" is used synonymously with compile, particularly with respect to parameter validation, object generation, and, optionally, varying out the experiment in a laboratory. Finally, FIG. 1 describes one embodiment, but other layouts and sets of panels may be utilized.

Types of Experiments

Unlike the computer systems and software packages that come with typical commercial laboratory instruments, the system and software of the present disclosure enables integration of different types of laboratory instruments. Therefore, the present system is able to remotely run a large variety of experiments, both singly and in any compatible combinations, including combinations that constitute a succession of experiments in either series or parallel. Such a capability is reflected on the interface. The system and software of the present disclosure may be advantageously configured to refuse to run physically nonsensical or dangerous combinations, e.g., creating a solid material and then attempting manipulate it with a liquid handling device. The enumeration of types of experiments and techniques in this disclosure is done to illustrate functionality of one or more embodiments with the explicit understanding that they will not be used to limit the scope or the meaning of the claims that follow.

Therefore, in one embodiment, the listing of experimental techniques includes at least two of the following types: synthesis, purification, amplification, quantification, and cell culture. In one aspect, the listing includes at least synthesis and purification. In one aspect, the listing includes at least amplification and quantification. In one aspect, the listing includes at least purification and cell culture.

In some embodiments, the listing can further include techniques other than quantification (non-quantification techniques). Non-quantification techniques can include, for instance, chromatography, microscopy, electrophoresis, spectroscopy, and volume or weight check. In a particular example, the listing can include at least nucleic acid or protein synthesis, nucleic acid or protein analytics, and nucleic acid amplification. Furthermore, experimental techniques may belong to multiple types, e.g., High Performance Liquid Chromatography (HPLC) is both a purification and quantification type of technique.

"Synthesis" refers to the production of an organic or biological molecule from starting materials without the use of a cell. Organic synthesis can be total synthesis or semi-synthesis. A total synthesis is the complete chemical synthesis of complex organic molecules from simple, commercially available or natural precursors. Total synthesis may be accomplished either via a linear or convergent approach. In a linear synthesis, several steps are performed one after another until the molecule is complete. The chemical compounds made in each step are called synthetic intermediates. For more complex molecules, a different approach may be preferable: convergent synthesis involves the individual preparation of several "pieces" (key intermediates), which are then combined to form the desired product. Semi-synthesis or partial chemical synthesis is a type of chemical synthesis that uses compounds isolated from natural sources (e.g., plant material or bacterial or cell cultures) as starting materials. These natural biomolecules are usually large and complex molecules. This is opposed to a total synthesis where large molecules are synthesized from a stepwise combination of small and cheap (usually petrochemical) building blocks.

In one aspect, the synthesis is biological molecule (e.g., nucleic acid or peptide) synthesis. Nucleic acid synthesis is the chemical synthesis of relatively short fragments of nucleic acids with defined chemical structure (sequence). Sometimes, the process is implemented as solid-phase synthesis using phosphoramidite method and phosphoramidite building blocks derived from protected 2'-deoxynucleosides (dA, dC, dG, and T), ribonucleosides (A, C, G, and U), or chemically modified nucleosides, e.g., LNA or BNA. Other methods are also available. Peptides can be synthesized by coupling the carboxyl group or C-terminus of one amino acid to the amino group or N-terminus of another. Due to the possibility of unintended reactions, protecting groups are usually necessary. Chemical peptide synthesis can be liquid-phase synthesis or solid-phase synthesis, without limitation. Non-limiting examples of molecule synthesis include DNA/RNA synthesis, organic synthesis (milligram to gram scale), and peptide synthesis.

"Purification" refers to a process for increasing the concentration of a desired substance (e.g., cell, compound, nucleic acid or peptide molecule) in a sample, which typically involves removing substances considered as impurity. Non-limiting examples of purification experiments include genomic DNA preparation, centrifugation, flow cytometry, fast protein liquid chromatography (FPLC), flash chromatography, HPLC (ion exchange), HPLC (reverse phase), RNA extraction, cDNA prep, protein extraction, solid phase extraction, thin layer chromatography (TLC), agarose gel electrophoresis, capillary electrophoresis, crossflow filtration (TFF), dialysis (preparative), fluorescence activated cell sorting (FACS), HPLC (normal phase), HPLC (preparative), immunoprecipitation, gas chromatography, gas chromatography mass spectrometry (GC-MS), liquid-liquid extraction, and supercritical fluid chromatography (SFC).

The term "amplification" as used here refers to the process of increasing the copy number of a nucleic acid fragment in a sample. The most well-known amplification method is the polymerase chain reaction (PCR) method, including quantitative real time PCR (qPCR) and digital droplet PCR.

"Quantification" refers to a process of ascertaining the quantity of a biological substance, in particular a protein or a nucleic acid molecule. Non-limiting examples include total protein quantification, fast protein liquid chromatography (FPLC), HPLC (ion exchange), HPLC (reverse phase), thin layer chromatography (TLC), UV/Vis spectroscopy, Western blot, microarray analysis, flow cytometry, HPLC (normal phase), and HPLC (preparative).

"Cell culture" encompasses experiments that grow cells or conducting experiments on a cultured cell, such as protein expression, apoptosis assays, mammalian cell culture, transfection, bacterial cell culture, yeast cell culture, colony picking, and electroporation.

"Non-quantification analytics" refers to any experiment that reveals certain characteristics (e.g., molecular weight, molecular identity, sequence, size, purity, pH, kinetics, charge, melting point, glycosylation status), other than mere quantification. Examples of non-quantitative analytics include, without limitation, analytical balance readings, epifluorescence microscopy, fast protein liquid chromatography (FPLC), flash chromatography, fluorescence kinetics, fluorescence polarization, fluorescence spectroscopy, fluorescence thermodynamics, HPLC (ion exchange), HPLC (reverse phase), light microscopy, MALDI mass spectroscopy, pH reading, polyacrylamide gel electrophoresis (PAGE), thermometer reading, thin layer chromatography (TLC), UV/Visual (Vis) kinetics, UV/Vis spectroscopy, UV/Vis thermodynamics, Western blot, volume check, agarose gel electrophoresis, atomic absorption spectroscopy, atomic emission spectroscopy, atomic force microscopy, capillary electrophoresis, circular dichroism (CD), confocal microscopy, dialysis (equilibrium), differential scanning calorimetry (DSC), DNA sequencing (next generation), DNA sequencing (Sanger), dynamic light scattering (DLS), electron microscopy, electrospray ionization (ESI) mass spectrometry, enzyme-linked immunosorbent assay (ELISA), HPLC (normal phase), HPLC (preparative), fluorescence in situ hybridization (FISH), gas chromatography, gas chromatography mass spectrometry (GC-MS), inductively coupled plasma mass spectrometry (ICP-MS), infrared spectroscopy, isothermal titration calorimetry (ITC), liquid chromatography mass spectrometry (LC-MS), melting point determination, microarray analysis, NMR (2D/structural), NMR (carbon), NMR (proton), patch clamp recordings, photostimulated luminescence (PSL), supercritical fluid chromatography (SFC), refractometry, scanning tunneling microscopy, solubility testing, surface plasmon resonance (SPR), tandem mass spectrometry (MS-MS), total internal reflection fluorescence (TIRF) microscopy, and X-ray crystallography.

In some aspects, the listing further includes one or more of the following experiments: autoclaving, buffer prep, liquid handling, lyophilization, rotary evaporation, speedvac concentration, vacuum filtration, viral prep, *Arabidopsis* study, bio-reactor, bomb calorimetry, *C. elegans* study, crystallization, *Drosophila* study, flow chemistry, plasmid construction, sonication, tissue homogenization, ultracentrifugation, microwave reactions, and molecular cloning.

Conversion and Display of Scripts

Figure 2:
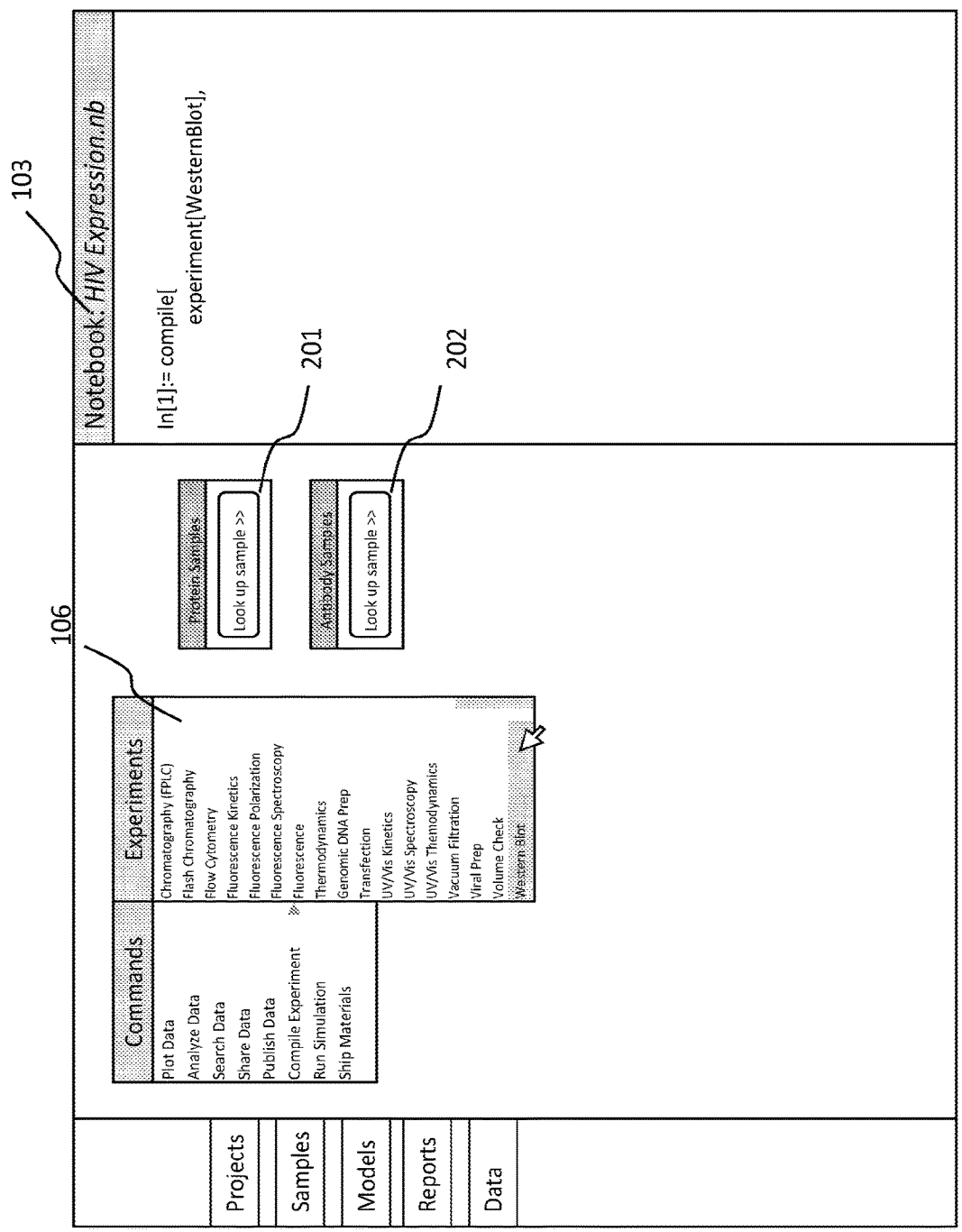
FIG. 2 shows that the user, after selecting an experiment type, is presented with an interface to choose samples.

On the interface 100, the user can give instructions to the system, such as by making a desired selection in the main area 102. As shown in FIG. 2, the instruction is to run a "Western Blot" experiment. Such instructions will be translated into computer code for instructing corresponding instruments to carry out the experiments. In some embodiments, the computer code is in the form of a scripting language. In one aspect, the scripting language is Symbolic Lab Language (SLL).

SLL is developed based on the Mathematica® language. On top of the user-friendly syntax and comprehensive data manipulation and visualization functionalities provided by Mathematica®, SLL further includes functions, objects, and knowledge representations specifically designed for the life sciences. As used herein, "object" without further modification refers to a data structure and/or a function unless otherwise stated. Also importantly, modules have been built for interfacing with a large number of laboratory instruments to enable efficient instrument management and data communication.

SLL can be supported on a variety of databases with varying performance tradeoffs. As used herein the term "database" refers to a structured set of data held in a computer, especially one that is accessible in various ways. Non-limiting examples of types of databases include relational, graph, probabilistic, XML, SQL, XQuery, and NoSQL. Non-limiting examples of databases include PostgreSQL, MySQL, Oracle Relational DBMS, MongoDB, DB2, and Cassandra.

SLL offers an objective system for querying, manipulating, and displaying experimental results. The results of each experiment, including data points involved in plots (such as chromatographs or spectra, etc.), images (such as gels, blots, and microscope slides), and meta data (such as the date the experiment was performed, the reagents used in the course of the experiment, the instrument utilized to conduct the experiment, etc.) are represented as objects and that are processed and inserted into a database and linked together. In one embodiment this is accomplished by means of pointers or "keys" which can be used to access such related yet conceptually distinct information. This is particularly powerful when one object is related to multiple heterogeneous experiments, e.g., an instrument object is linked to all experiments that utilized that instrument, regardless of exact experimental technique, sample type, etc.

This setup allows scientists to easily and compactly share data across multiple notebooks and teams without losing quantitative precision or any associated details.

Furthermore, a computational system of data objects per SLL allows one to manipulate large sets of experimental data abstractly, by giving one the ready ability to write scripts that process these objects as inputs and process them in an algorithmic manner.

To more clearly illustrate the SLL and some of the concepts of the disclosed invention exemplified by SLL's implementation, the following are non-limiting examples of SLL objects, functions, and their usage.

Example of a data object: data[index,<type>], e.g., data[44, NMR] can point to the 44th nuclear magnetic resonance (NMR) experiment performed in the lab, and data[1023, MALDI] refers to combined results from the 1,023rd matrix-assisted laser desorption/ionization (MALDI) experiment performed. The precise indexing scheme is not important—neither chronological ordering is necessary nor is any particular symbolic identifier, e.g., a user defined string can be used to identify an object, so long as it is sufficient for the system to reliably ascertain the intended object.

Examples of Functions info[ ]—calling info on a data object, e.g., info[data[44, NMR]], connects to the database and then returns a list of all data associated with that experiment. In some embodiments info is configured to locally cache that data such that further calls to info[ ] will automatically reference the locally cached copy (for faster execution times) rather that connect to the database; and inform[ ]—calling inform on a list of all data associated with the experiment in the form of replacement rules will: check to see if that data has already been inserted into the database and, if so, return the data[ ] object previously inserted and otherwise will insert that data into the database and return a new data[ ] pointer to that object.

SLL also includes functionality for tracking and querying the complete history of laboratory samples. Examples of tracked information include: information about source materials; preoperative information from processes involved in its creation; its present properties, such as experiments it which it has been used; quality assurance (QA) information; information regarding its properties, such as volume, concentration, and pH; information regarding its innate properties, such as chemical composition, and physical location in the laboratory or facility.

Additional Examples of Objects

Objects representing physical samples: sample["sample name,"<type>], e.g., sample["Nearest Neighbor Strand 4," "DNA"] encapsulates information involving that sample such as materials involved in its creation, dates, and experimental results from production experiments involved, attributes of the sample, such as its volume, pH, concentration, and its physical location in the lab (where it is stored); or group["name of group"], e.g., group["Nearest Neighbor Strands"] refers to a collection of samples that you wish to manipulate in bulk. Groups can refer to any size collection of samples, and samples can be members of multiple groups.

A protocol object is generated pursuant to the execution of an experiment function. For instance, executing the command: ExperimentHPLC[sample["Crude Nearest Neighbor Sequence 5"], Method→IonExchange, FlowRate→3 Milli Liter/Minute] will produce a protocol object protocol [12345, HPLC] that is utilized by the system to direct and coordinate the production of a new physical sample (and corresponding sample object) that results from the purification of crude nearest neighbor sequence 5 via preparative ion exchange HPLC run at 3 milliliter per minute flow rates. In this way experiment functions are used to direct physical activity within a laboratory from within a lab notebook. In the preferred embodiment this is mediated by protocol objects, but other object configurations may be utilized. Further, in the preferred embodiment the protocol object is returned to the user.

In the preferred embodiment protocol objects, which represent experiments, are placed in a queue to await processing into commands and tangible actions in an actual research facility. Initially, executing any experiment function from within a notebook starts by adding samples and instructions involved in that process to a process queue. A process queues is a queue of experiments awaiting physical execution within a laboratory. In some embodiments management of a process queue is performed by a human while in other embodiments it is managed by computer algorithms or a hybrid of human and algorithmic decision making. After an experiment has been removed from the queue and executed, the user who originally initiated the experiment will be informed that the experiment has been completed, and will receive the results from that experiments (samples and/or data). In the preferred embodiment the user receives computer objects representing the samples and/or data and which allow the user to access relevant information about the results.

Furthermore, the actual instructions for performing a specified experiment (typically referred to in the art as an experiment protocol, hence the name "protocol object") are generated when the protocol object is taken off the queue and processed by the orchestration module. The orchestration module may be located in the laboratory where the experiment is to be performed, on a remote server, or elsewhere, so long as it is capable of communicating with the laboratory where the experiment is to be performed. When a human operator conducts a given experiment in the lab, relevant aspects of the generated instructions are presented to her as dynamic interactive checklists on a computer, portable tablet, smartphone, or another remote device capable of information sharing. As the operator goes through the process, these checklists will present fields to mark completion of each step, enter information such as filenames from instruments, standard observations, or even detailed notes when running into unforeseen difficulties. Due in part to the programmatic linkage of the generated instructions with the experiment parameters, physical sample inputs, environmental sensors, and other contextual information, the preferred embodiment also supports integration with specific instrument programs and physical tracking devices, such as bar codes, or radio-frequency identification tags, for tracking source materials employed in the course of the experiment and automatically linking that information to output samples and any resulting data. Further, the generated instructions themselves may be dynamically altered in response to information received from the lab. One skilled in the art will readily appreciate that certain steps assigned by the orchestration module to humans may also be assigned to robotic systems, alone or in tandem with humans, and such variations are also claimed.

Once instructions received at the user interface 100 are received and converted to computer scripts, the scripts can be displayed in the script panel 103. Such display serves multiple purposes. First, the user can compare the script with the user's instructions through the graphical interface on the left to confirm the instruction. Second, a user that is not familiar with the scripting language, e.g., SLL, can familiarize herself with the language by looking at the dynamically generated script based on the user's inputs in the graphical user interface. Third, the user can directly enter scripts in the script panel, or modify existing ones. As direct writing of scripts provides better flexibility and more control, giving a user direct access to the script can further empower the user. In the preferred embodiment the script panel is part of an interpreted development environment, for example that found in Mathematica, and the scripts are written in an interpreted computer language, for example the Wolfram Language based SLL. Other embodiments support other interpreted and compiled languages, for example SciPy and NumPy, as well as compiled and interpretive development environments.

In some aspects, when a user directly enters a script command at the script panel or modifies an existing one, the addition or change can be reflected in panel 102. For instance, if the user change the script that is shown in panel 103 from "experiment[WesternBlot]" to "experiment[Transfection]," rather than prompting the user to select protein samples and antibody samples, the interface will prompt the user to identify DNA samples and cell samples.

Sample Selection

Once an experiment type is selected in 106, the system will determine types of samples needed for the experiment and prompt the user to select appropriate samples. For instance, in the example of FIG. 2, the user clicks on "Western Blot" and the system then determines that such an experiment requires protein samples and antibody samples, and accordingly displays two input areas, 201 and 202, for the user to identify samples. In some embodiments the system will only determine the sample type and other parameters upon attempted execution of a function.

Samples can be sent to a facility, created from scratch, or identified from a data source on a computer as a sample that already exists within the overall system. When creating a sample (or entering a new sample into the data source), the user has the option to annotate, i.e., specify values of, various properties of the sample, such as concentration, volume, purity, date of generation, and/or name of lab or technician preparing the sample, without limitation. In the preferred embodiment the system is configured to require annotation of certain properties, for example to ensure that information essential to potential subsequence experiment execution is entered.

Depending on the type of sample or the experiment, certain properties of the sample may be required for experiment design. For instance, the pH and concentration of a protein sample can be required for an HPLC experiment. If the pH and concentration are not provided by the user, the system will need to deal with the absent data accordingly. For instance, the system can add a step to determine the pH and concentration of the sample and then adjust them to optimal values, if needed. Prior to or absent such determination, the system can use a pre-determined default value. The system can also prompt the user to enter missing sample property values.

In some aspects, the system arranges a determination step for important parameters (e.g., pH, concentration, volume) whether or not such information is provided for the samples by a user. This is useful in the event that the user-provided information is not accurate or if the information has changed, e.g., during shipping. The system may also cross-check related parameters or dependent properties in order to assure internal consistency.

Figure 3:
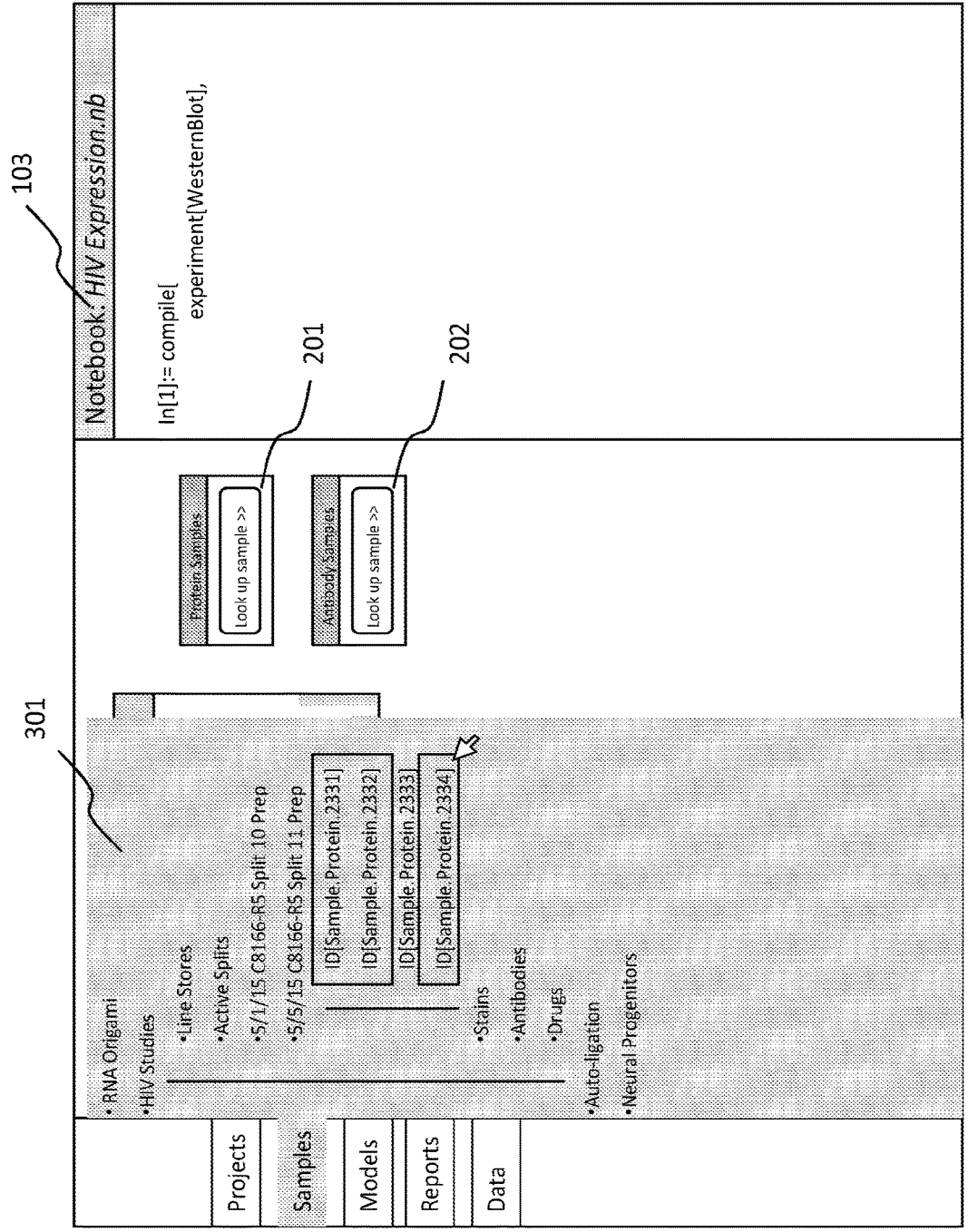
FIG. 3 shows an interface for the user to choose samples to be run in an experiment.
Figure 4:
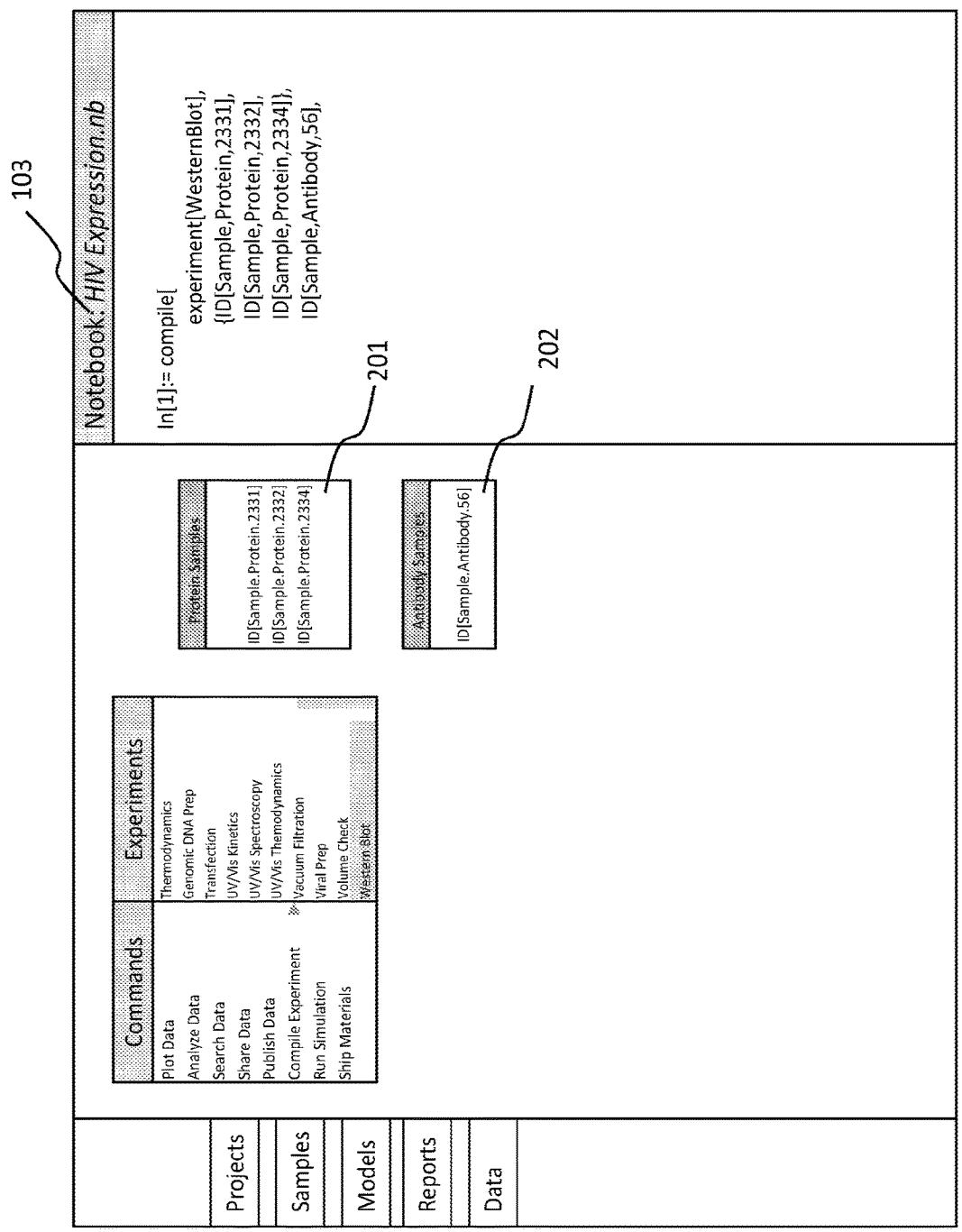
FIG. 4 shows that the samples are chosen for the experiment.

When selecting samples for the experiments, as shown in FIG. 3, the user can simply highlight desired samples from menu 301, and drag and drop to the appropriate areas (201 or 202). As described above, such a selection of sample will trigger generation of corresponding computer script, which will be displayed in script panel 103.

In some embodiments, not illustrated in the figures, a user can opt to select samples first, followed by selection of experiment type. In this scenario, when presenting experiment types to the user, the system can filter the list of experiment types according to the sample type. For example, Western Blot will not be included in the list if a DNA sample is selected. A user may also directly input scripts without the assistance of the graphical aids.

Experimental Parameter Adjustment

Once the experiment type and samples are identified, the system will then present an interface for the user to set experimental parameters (see, e.g., panel 501 in FIG. 5). It is noted that the exact experimental parameters presented for user entry and/or adjustment not only depends on the experiment type, but can also be affected by the sample(s) selected.

When presenting experimental parameters for the users to enter or adjust, the system can also determine a subset of parameters for which user input is preferred, desired, or required. For example, for a Western blot experiment, the system can determine that staining time and washing time are better determined by the user than for other parameters. Accordingly, these two items may be highlighted to attract user attention.

In some embodiments, the system further includes one or more desired experimental results for a user to determine, in addition to experimental parameters. In one aspect, the desired result is the desired concentration, desired purity, desired weight (or copy number) of a product generated from an experiment. Once the interface receives an input from the user concerning such a desired result, the system can then calculate suitable experimental parameters in order to achieve the desired results. The desired experimental result can also be a parameter.

Parameter Resolution

The system of the present disclosure, in some scenarios, ensures that all parameters of an experiment are determined (alternatively termed "resolved") and saved for future reference before the experiment is actually carried out. There are at least three benefits from such an effort. First, once the experiment is designed with the parameters resolved, the user will have the confidence that the experiment will be carried out as intended, without the need for further input, adjustment, or correction from the user (subject to certain critical failures like a sample spoiling during shipment). Second, the experimental outcome will be reproducible because parameter resolution eliminates any parameter ambiguity material to experiment execution, thus eliminating a major source of experimental inconsistency. Third, future experiments can either copy or leverage the samples and underlying parameters, making data and samples generated in the distant past as useful a basis for further experimental inquiry as data and samples generated yesterday because no contextual knowledge regarding the experiment has been lost. In other words, the present technology can achieve high predictability and reproducibility in the conduct of laboratory experiments, as further illustrated below. Further, it is noteworthy that this programmatic identification and resolution of experimental parameters is only possible in an integrated electronic system; without a machine readable definition of a given experiment, a computer would be unable to understand what is being requested and therefore unable to assist in determining whether the request is well formed and sufficient.

Irreproducibility has long plagued the scientific community, particular with respect to the life sciences. One type of irreproducibility comes from the effort of scientists attempting to reproduce an experiment reported in scientific journal. For example, in an effort to quantify this irreproducibility, an experiment was conducted as ascertain major causes of the problem (Vasilevsky et al, PeerJ. 2013 Sep. 5; 1: e148). It was hypothesized that some of the inconsistencies stemmed from a lack of "identifiability" of reagents, tools, and model systems used. The report found that 54% of these resources were not uniquely identifiable, making it difficult to impossible for peers to reproduce the exact test conditions.

Another type of irreproducibility arises when someone repeats an experiment done by the same or another person earlier in the same laboratory or organization. For instance, it was reported recently that "More than 70% of researchers have tried and failed to reproduce another scientist's experiments, and more than half have failed to reproduce their own experiments." (Nature 533, 452-454 (26 May 2016)). At least one reason for such high irreproducibility is the ambiguity in setting and/or recording experimental parameters or conditions. By contrast, in some embodiments of the presently disclosed technology, all experimental parameters or conditions (sometimes termed "options") are resolved prior to execution of the experiment. This process can be referred to as "option resolution" or "parameter resolution."

One aspect of parameter resolution concerns parameter identification, that is, what parameters and conditions need to be determined before an experiment is executed. Another aspect concerns making determinations for these parameters and conditions, including which determinations may take input from a user. Yet in another aspect, after receiving a user input, the system inspects the input and makes recommendations, warning, or automatic adjustments where needed. Each of these aspects is described in further detail below.

The parameters and conditions that are determined for an experiment prior to execution of the experiment are typically more extensive than when a similar experiment is conducted in a conventional manner. Take HPLC as an example. In a conventional HPLC experiment, prior to starting the HPLC experiment, the technician may determine what column to use, the concentration and volume of the sample, the buffers, and the flow rate. Other parameters or conditions, however, are to a great extent left undecided or are part of the tacit unrecorded knowledge of the person physically conducting out the experiment. Furthermore, recording parameters is important in scientific inquiries because one often does not know what will be important or impactful in the future, so selective or haphazard recording runs a very high risk of omitting valuable knowledge.

One type of parameter that is typically not specified in a conventional experiment is instrument preparation or calibration. For instance, in the HPLC example, the parameter "flush frequency," which specifies the frequency at which extra flush runs will be inserted between samples, is typically decided by the tradition of a particular laboratory or the habit or training of a technician. Again, this important information is not written down or captured in a way that is linked to a specific experiment even though it can have a large impact. For example, internal experiments have shown that certain flush frequencies can introduce enough variability within a single experiment so as to render the resulting data useless, yet this vital piece of information is not recorded in traditional systems. Another such example is "standard after flush" which determines whether a standard is run after each extra flush run. A further example is the amplifier gain on the photodiode in a flow cytometer, a parameter which is often set when the instrument is first installed and then forgotten thereafter, despite the large impact it has on experimental observations. In one embodiment of the present disclosure, however, during the experiment design step, such instrument preparation or calibration parameters need to be identified and values determined.

Another type of parameter that is typically not determined in a conventional experiment is post-experiment care. One such example is the shutdown method or clean up flush for a HPLC experiment. In one embodiment of the present disclosure, during the experiment design step, such an instrument post-experiment care parameters need to be identified and values determined.

Yet another group of parameters that are typically not determined in a conventional experiment are parameters for operations or analytics that can be performed during the experiment. Some of the operations or analytics may depend on certain output from the experiment. For instance, during a HPLC experiment, various fraction collection parameters (e.g., start time, end time, collection mode, maximum collection volume) may be determined or adjusted ad hoc. In one embodiment of the present disclosure, however, parameters can be determined prior to sample loading. For instance, the user may be asked to input a standard (e.g., peak start threshold, which defines the signal threshold for detecting a peak), which is then used to determine the fraction collection parameters.

It may be common that a user is not familiar with many of the parameters that the present system is set out to resolve. Therefore, in some embodiments, the system of the present disclosure assists the user by including or presenting recommended values for the parameters. In one embodiment, the recommended value for a parameter is predetermined in the system. For instance, for an analytical HPLC, the system by default sets the injection amount to 1 nanomole absent explicit user instruction; for a preparative HPLC, the system defaults the injection amount to 50 nanomole. In another example, the system dynamically defaults the temperature parameter to 45 Celsius or 25 Celsius depending on the user's choice of reverse phase or ion exchange HPLC. As with other parameters, the system selected temperature value may be overridden by the user. In the preferred embodiment the system only requires that the user specify parameters that either the system cannot resolve on its own or where the user wishes to override system's own resolved values, thus allowing for a very compact script. For example, in SLL the HPLC experiment function has 43 parameters: Inform, Accept, Options, Scale, Collect Fractions, Injection Volume, Flush Frequency, Standard After Flush, Injection Amount, Column, Instrument, Type, Buffer A, Buffer B, Buffer C, Batch Standard Injection Volume, Batch Standard Sample, Batch Standard Method, Flush Method, Shutdown Method, Gradient Standard, Gradient Standard Injection Volume, Temperature, Flow Rate, Detection Wavelength, Gradient B, Gradient C, Gradient Start, Gradient End, Gradient Duration, Equilibration Time, Flush Time, Gradient Method, Fraction Collection Start Time, Fraction Collection End Time, Fraction Collection Mode, Max Fraction Volume, Absolute Threshold, Peak Slope, Peak Slope Duration, Max Collection Period, Peak End Threshold, and Fraction Collection Method, all of which the system can resolve. Thus, in the preferred embodiment a user who does not desire to override any system recommended settings could simply enter:

ExperimentHPLC["Sample 1"]

rather than the rather unwieldy and intimidating:

ExperimentHPLC["Sample 1", Inform→User Value, Accept→User Value, Options→User Value, Scale→User Value, CollectFractions→User Value, InjectionVolume→User Value, FlushFrequency→User Value, StandardAfterFlush→User Value, InjectionAmount→User Value, Column→User Value, Instrument→User Value, Type→User Value, BufferA→User Value, BufferB→User Value, BufferC→User Value, BatchStandardInjectionVolume→User Value, BatchStandardSample→User Value, BatchStandardMethod→User Value, FlushMethod→User Value, ShutdownMethod→User Value, GradientStandard→User Value, GradientStandardInjectionVolume→User Value, Temperature→User Value, FlowRate→User Value, DetectionWavelength→User Value, GradientB→User Value, GradientC→User Value, GradientStart→User Value, GradientEnd→User Value, GradientDuration→User Value, EquilibrationTime→User Value, FlushTime→User Value, GradientMethod→User Value, FractionCollectionStartTime→User Value, FractionCollectionEndTime→User Value, FractionCollectionMode→User Value, MaxFractionVolume→User Value, AbsoluteThreshold→User Value, PeakSlope→User Value, PeakSlopeDuration→User Value, MaxCollectionPeriod→User Value, PeakEndThreshold→User Value, and FractionCollectionMethod→User Value]

where "User Value" denotes where a user would specify the desired parameter value. Importantly, all parameter values are saved for future reference, regardless of whether a parameter is determined by the system or a user. This means that it is easy for a user to rerun the exact same experiment in the future, as one can simply copy the saved parameter values. This can be done automatically by the system or manually by the user. The ability to flexibly specify all the parameters of an experiment in easy to read script that is compact yet computationally complete represents a powerful advancement in the art.

In another embodiment, the recommended value for a parameter depends on another parameter. For instance, in one embodiment the system can determine an appropriate detection wavelength once the system is resolves the sample type. For a sample determined to be DNA, the system suggests that the detection wavelength parameter be set to 260 nm; for a sample determined to be protein, the system suggests a detection wavelength of 280 nm.

In another embodiment, the recommended value for a parameter is not a fixed value but rather a formula or function that takes input from another experiment or another portion of the same experiment. In this context, it is noted that in some embodiments, the system is configured to monitor performance of the experiments, and the information collected during the monitoring can be used to help determine or adjust experimental parameters in another experiment or another portion of the experiment.

In one scenario, the information used to determine or adjust one or more experimental parameters is historical information of a sample, e.g., from an earlier/upstream experiment. For example, when the sample is a cell sample and the system has data relating to the growth rate of the cell type in the sample, then the historical growth rate information can be used to adjust experimental parameters to ensure that the cells grow at a suitable rate.

In another scenario, the information used to determine or adjust one or more experimental parameters is historical information of an instrument. An instrument may be calibrated periodically. The calibration results can be used to guide adjustment of experimental parameters. The results of other experiments run on the instrument can also be used to adjust and optimize the parameters.

Figure 6A:
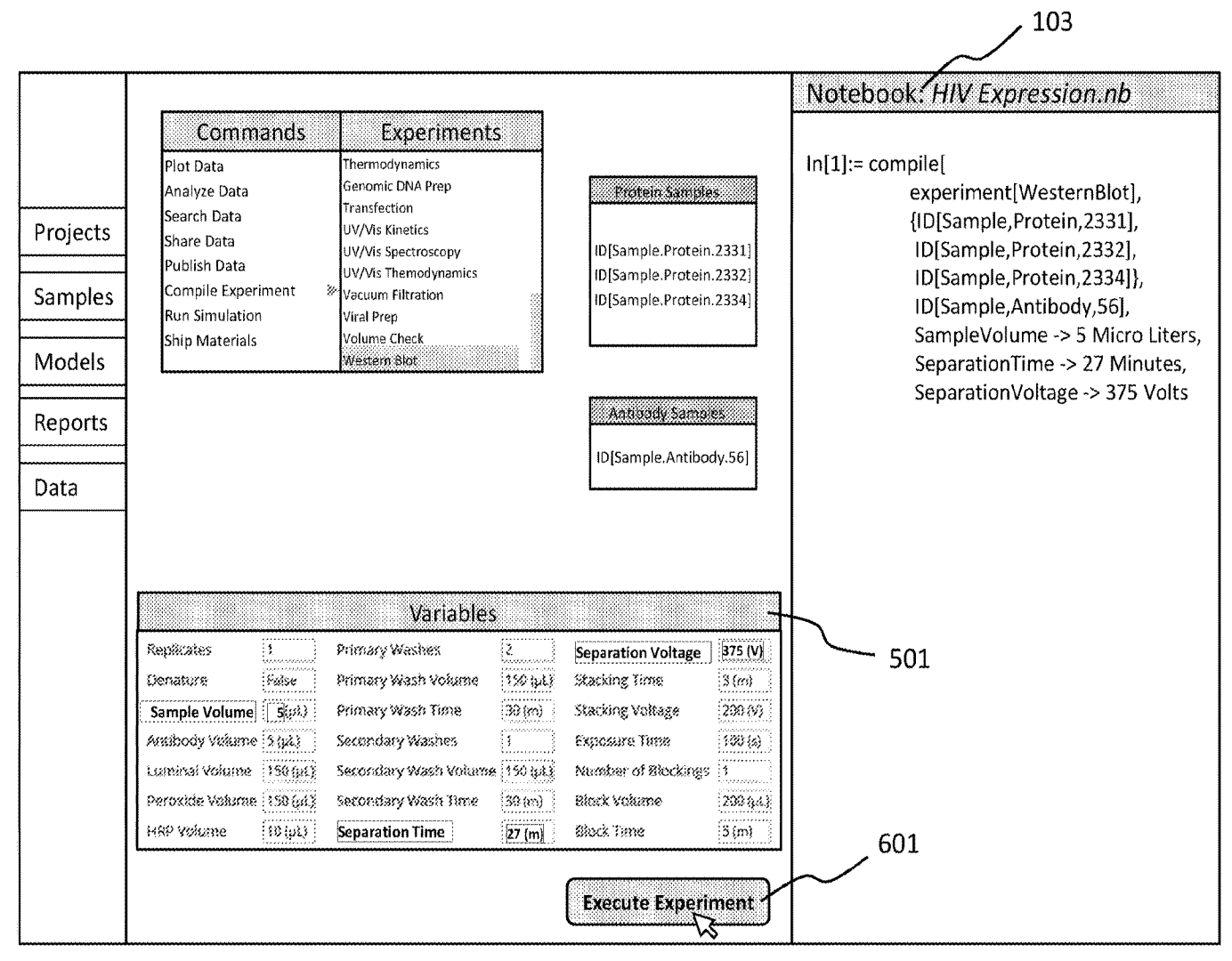

The recommended values for the parameters can be used to automatically set these parameters absent further user input, in one embodiment. Such automatically populated values are illustrated in FIG. 5. Nevertheless, the user may be allowed to adjust any of the parameters as desired, even though the system may impose certain limitations. In FIG. 6A, for instance, the user elects to adjust the values for Sample Volume, Separation Time, and Separation Voltage, for the selected Western Blot experiment. Upon receiving these values, in one embodiment, the system evaluates the validity of these values. In some embodiments only a subset of parameters are presented to the user for consideration.

Given that some of the parameters have dependencies on other parameters, in some embodiment, the system checks the validity of the values in an order that observes such dependencies. For example, with respect to the three parameters adjusted in FIG. 6A, the system can first check whether the values for Sample Volume, Antibody Volume, Luminal Volume, and Peroxide Volume are within optimal ranges, recommended ranges, or acceptable ranges. To this end, it is noted that the optimal ranges, recommended ranges, and acceptable ranges for a parameter can be determined by the system as the system determines a recommended value for the parameter.

Further, the resolution of some parameters depends upon the value of other parameters which themselves need to be resolved. Various parameters may be resolved based upon a formula or function, thus full resolution may depend upon the resolution of a complex series of interrelated functions. It is important to note that in the preferred embodiment the logic for this need not necessarily be explicitly programmed into the system, rather, resolution is naturally handled by the sequential resolution of options, analogous to the resolution of recursive function calls in computer science.

Then, the system evaluates the values for Separation Time, Separation Voltage, Stacking Time and Stacking Voltage for their suitability for this particular experiment provided that it has the Sample Volume, Antibody Volume, Luminal Volume, and Peroxide Volume which have already been evaluated in the previous step. In the example shown in FIG. 6B, the system determines that the user-provided Separation Voltage is too high and thus displays a warning in the right hand side panel.

Figure 6B:
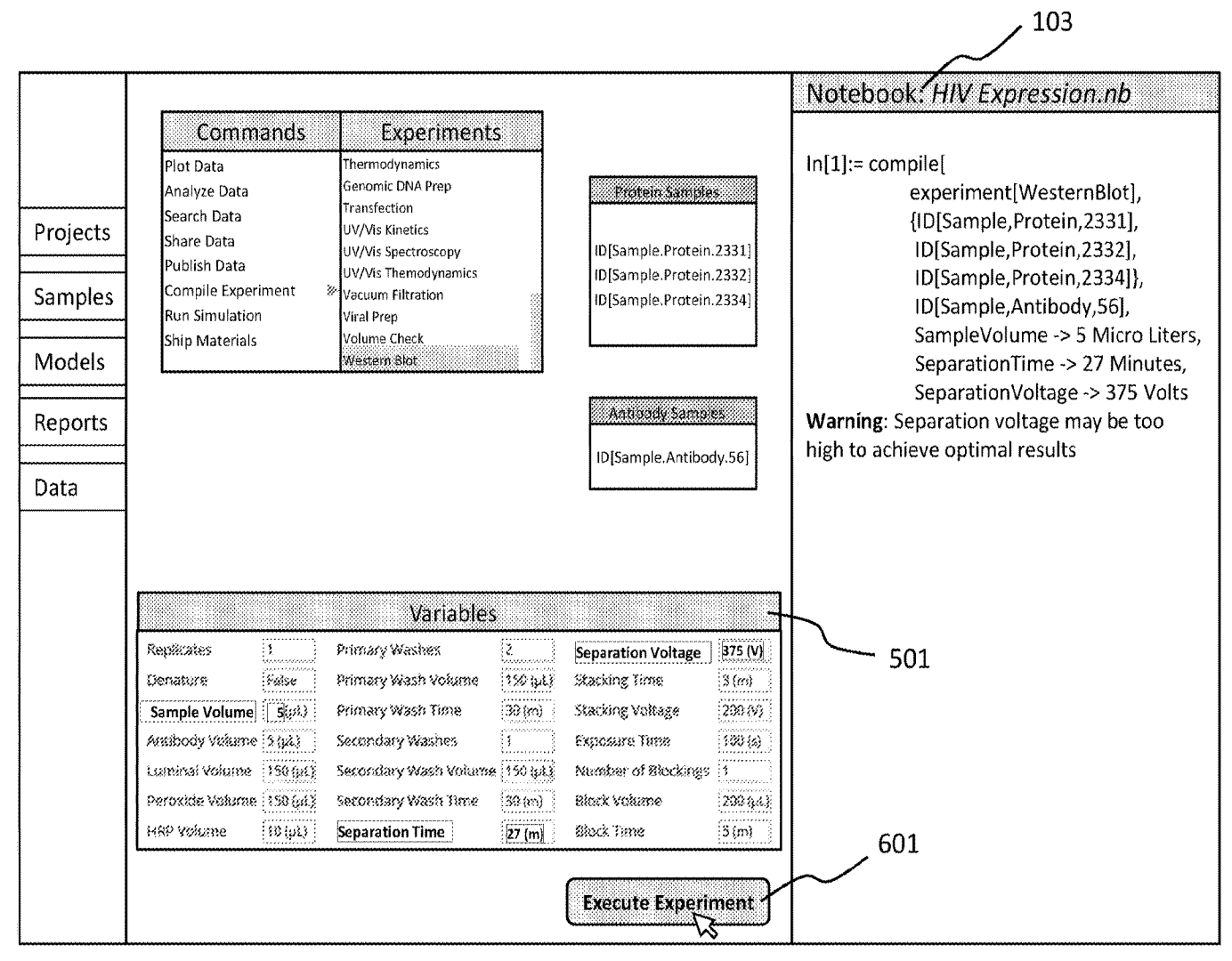

In accordance with certain embodiments of the present disclosure, after the users completes the design of the experiment (e.g., clicking the "Execute Experiment" button on the interface of FIG. 6A or 6B), no more input is needed from the user for completing the execution of the experiment. In one embodiment, the input refers to information concerning manipulation of the sample. In one embodiment, the input refers to information concerning selection of reagents. In one embodiment, the input refers to information concerning conditioning, preparation, settings, or calibration of an instrument. In one embodiment, the input refers to information concerning collection of an output sample from the experiment. In one embodiment, the input refers to information concerning further processing of an output sample from the experiment. In one embodiment, the input refers to information concerning setting environmental parameters for the experiment. In one embodiment, the input refers to information concerning storing or displaying experimental results.

Receiving and Loading Samples

As the presently disclosed system can enable computationally complete descriptions of experiments, the experiments can be performed remotely by either machines or a combination of machines and humans, thus implementing a version of the lab-in-the-cloud concept. Therefore, in addition to working through a computer interface, in some embodiments, a user only needs to send samples to where the instruments of the system are located (i.e., the lab) without taking other physical actions.

The samples can be sent before or after information about the samples in entered into the system. Typically, however, at least each sample already has some basic information before it is received at the lab. For instance, each sample is given a name or identification number, and preferably the sample type (e.g., DNA sample, protein sample, cell line). In some instances, additional information, such as concentration, pH, data of preparation, molecular weight, is also entered in the system.

Once the samples are received at the lab, the samples can be examined before being placed in storage or loaded into the instruments. The examination can include measurement of concentration, temperature, volume, weight, and/or pH, without limitation. In the event there is discrepancy with information provided by the user, adjustments can be made, or flags are raised concerning quality or stored properties of the samples.

In some embodiments, the experimental parameters for an experiment are adjusted based on such measurements. In one scenario, the measured results are different from what has been provided by the user on the interface. This can be caused by, e.g., sample degradation or loss of humidity, during transportation. In another scenario, the system may have used default values in the experimental design when certain parameters were not set by the user.

Compound Experiments

The ability of the presently disclosed laboratory system is not only reflected in its ability to automate a large variety of both simple and complicated experiments, but also highlighted in its ability to design and execute compound experiments. A "compound experiment" refers to an experiment that includes at least two component experiments, the output of one of the component experiments being the input sample of the other component experiment. Further, the two component experiments may differ in type, e.g., molecule synthesis, purification, amplification, quantification, cell culture, and analytics. In some embodiments, a compound experiment includes at least three different types of experiments. In some embodiments the system is capable of supporting compound experiments with arbitrarily many different experiments and is limited only by available resources. Portions of the compound experiment may occur over time as one portion depends on the output or results of another portion. Portions of the compound experiment may proceed in series or in parallel with each other. The execution of a portion of a compound experiment may depend upon the user first reviewing the results of another portion of the compound experiment and adjusting the compound experiment as desired. A compound experiment need not be fully specified before execution begins; for example a user may create or extend a compound experiment by adding additional component experiments over time. In practice, certain embodiments are capable replicating the overall experiment detailed in any life sciences publication composed of analytical chemistry, cellular biology, and/or molecular biology techniques.

One example of a compound experiment includes nucleic acid synthesis (synthesis), followed by nucleic acid purification (purification), nucleic acid quantification (quantification), then nucleic amplification (amplification), and then sequencing (analytics). In another example, a compound experiment includes protein expression (cell culture) followed by protein purification (purification), and ELISA (quantification).

Once one component experiment in a compound experiment is completed, the system collects an appropriate output sample from the component experiment, optionally followed by suitable sample analytics. For example, for a polynucleotide example, the concentration and volume can be checked. If needed, concentration, dilution, pH adjustment, etc. can be carried out. Subsequently, this output sample is transferred to the instruments for the next component experiment. The experimental parameters for the next component experiment can also be adjusted on the fly according to the sample analytics and follow-up adjustments.

A compound experiment can further include one or more component experiments that "branch in" to or "branch out" of a base compound experiment. A branch-in component experiment generates a sample or data that, together with the output sample and/or data or a second component experiment, form input to a third component experiment. By contrast, a branch-out component experiment shares input sample or data with a second component experiment, that has been generated from a third component experiment. Data collected at each component experiment can be used to adjust experimental parameters of any other component experiment, either automatically or based upon user input.

Parameter resolution in designing a compound experiment may need to take into consideration the relationship between the individual experiments within the compound. See the following example of a compound experiment with 7 techniques:

Phase I:
1) ExperimentDNASynthesis=>generates DNA samples
2) ExperimentHPLC (Ion Exchange)=>purification of samples generated in (1)
3) AnalyzePeaks=>analyze peaks generated in (2) and select fraction samples based on those peaks Phase II:
Now take the fraction samples selected in (3) and perform the following four experiments in parallel, or in any order the user desire, each generating data for further analysis:
4) ExperimentHPLC (Analytical)
5) ExperimentPAGE
6) ExperimentMassSpectrometry
7) ExperimentAbsorbanceQuantification Phase III:
Perform any one or more analysis as appropriate, in any order:
8) AnalyzePeaks
9) PlotPAGE
10) PlotMassSpectrometry
11) AnalyzeAbsorbanceQuantification In this example, a particular consideration for parameter resolution is that the ExperimentHPLC experiment of step (4) can inherit many parameters from ExperimentHPLC run in step (2). Therefore, less or no input is required from the user concerning step (4) once the parameters are resolved for step (1). Advantageously, this also reduces the opportunity for error caused by inadvertent variation in parameter values between (1) and (4), as might occur in a manual setup where many parameter values are not explicitly considered or recorded. Further, upon the processing and analysis of the above steps, one or more of the following experiments can be performed on the output sample:
12) ExperimentAbsorbanceThermodynamics
13) ExperimentFluorescenceKinetics
14) ExperimentTransfection Note that the above compound experiment was not pre-configured by an expert and a user may alter it in any way or do something else entirely. Any combination that is physically permissible may be executed on the disclosed invention, which distinguishes it from, e.g., high throughput screening systems. The difference in capability is analogous to a general purpose computer versus a calculator; the flexibility and generalizability of the disclosed embodiments permit previously impossible capabilities. As another example, the following was taken from the methods section of a paper published in Nature Biotechnology, "The *Escherichia coli* K-12 strain BW25113 (genotype: F−, Δ(araD-araB)567, ΔlacZ4787(::rrnB-3), λ−, rph-1, Δ(rhaD-rhaB) 568, hsdR514) was used to generate the proteome map for all 22 conditions. Mutant strains with either the rimL, rimJ or rimI gene deleted were taken from the KEIO collection. Correctness of the deletions were checked by PCR. Additionally, the proteome for the glucose and LB condition was also determined for the strains MG1655 (genotype: F−, λ−, rph-1) and NCM3722 (genotype: F+)." Alexander Schmidt et al., *The quantitative and condition-dependent Escherichia coli proteome*, Nature Biotechnology 34, 104-110 (Dec. 7, 2015). This can be represented in SLL as:

Strains
  baseLine=model["BW25113",Cells];
  rimLLine=model["BW25113ΔrimL",Cells];
  rimJLine=model["BW25113ΔrimJ",Cells];
  rimILine=model["BW25113ΔrimI",Cells];
  altCellLines={model["MG1655",Cells],model["NCM3722",Cells]};

Primers
  rimLFowardPrimer=model["rimLFoward",Oligomer];
  rimLReversePrimer=model["rimLReverse",Oligomer];
  rimLBeacon=model["rimLBeacon",Oligomer];
  rimJFowardPrimer=model["rimFoward",Oligomer];
  rimJReversePrimer=model["rimJReverse",Oligomer];
  rimJBeacon=model["rimJBeacon",Oligomer];
  rimIFowardPrimer=model["rimIFoward",Oligomer];
  rimIReversePrimer=model["rimIReverse", Oligomer];
  rimIBeacon=model["rimIBeacon",Oligomer];

Experiments
  ExperimentcDNAPrep[{rimLLine,rimJPrimerSetrim-IPrimerSet}, PBSSample→model["PBS", StockSolution], LysisSolutionSample→model["ABIcDNAPrepLysis",Chemical], MediaVolume→150 Micro Liter, WashVolume→100 Micro Liter, AnnealingTemperature→45 Celsius]
  protocol[123123, cDNAPrep]
  lysisSamples=SamplesOut/.Info[cellPrep]

{sample[12451, Lysate], sample[12452, Lysate], sample[12453, Lysate]}
ExperimentqPCR[lysisSamples, FowardPrimers→{rimLFowardPrimer, rimJFowardPrimer, rimIFowardPrimer}, ReversePrimers→{rimLReversePrimer, rimJReversePrimer, rimIReversePrimer}, Beacons→{rimLBeacon, rimJBeacon, rimIBeacon}, TemplateVolume→2 Micro Liter, ForwardConcentration→0.5 Micro Molar, ReverseConcentration→0.5 Micro Molar, BeaconConcentration→250 Nano Molar, DenaturationTemperature→95 Celsius, DenaturationTime→15 Second, AnnealingTemperature→60 Celsius, AnnealingTime→30 Second, NumberOfCycles→50]
protocol[123141, qPCR]
qPCRData=Data/.Info[protocol[123141, qPCR]]
{data[124584, qPCR], data[124608, gPCR], data[124602, qPCR]}
PlotObject[qPCRData].

Note that the disclosed invention was not designed specifically to execute the experiments in this paper. Rather, the flexibility of the system is highlighted by its ability to recreate any arbitrary experiment that utilizes the techniques that it supports, such as the experiment in this paper. Further, note that a number of parameters specified in the above SLL script are ambiguous in the source paper, something that is neatly resolved by the use of SLL scripting in combination with other aspects of the disclosed invention. Additionally, should one desire to rerun the same experiment in the future, a user need only reference an object associated with the experiment, e.g., protocol[123141, qPCR], to extract the exact parameters used for the experiment, thereby enabling the retrieval of a truly complete description of all steps taken in the experiment. Further, the function call invoking the qPCR experiment function is highly compact despite its completeness: for example ExperimentqPCR takes 42 parameters, yet only 12 were specified by the user, in this example to override system resolved defaults to match the paper. The system still saves the values used for all 42 parameters, be they user or system specified.

Additionally, the rest of the experiment disclosed in the paper can also be represented in SLL script, but is not done so here for brevity. The inventors are unaware of any system that is capable of such flexibility and scale. The fundamental point remains: the disclosed invention is highly flexible and capable of representing and executing a wide variety of experiments in pursuit of wide ranging scientific inquiry, including for basic research and development.

Generation of Experimental Protocols

In some embodiments, once the design of an experiment is completed and submitted by a user, the system generates an experiment protocol object based on the design, which can include the results from parameter resolution. Given the completeness of the parameter resolution in some embodiments, the protocol object can also be considered computationally complete, i.e., does not require further user input to describe the intended experiment, and serves as a set of instructions for instruments (and, optionally, technicians) to carry out the experiment.

To generate the experimental protocol used within the laboratory, in some embodiments the system processes the protocol object and resolves dependencies between steps, samples, reagents, and/or task scheduling (e.g., parallelism, availability of equipment, potential bottlenecks, physical distance between instruments in lab, location of relevant samples, etc.) to generate an experimental protocol to be followed in the lab. This resolution may require information not available to the portion of the system that created the protocol object, e.g., a user's local computer. This experimental protocol may include machine code for controlling robots and/or instruments, including API (application program interface) calls, as well as itemized instructions to be performed by a human as needed. In some embodiments the experimental protocol is generated and included in the protocol object when the protocol object is created. In the preferred embodiment the experimental protocol is created when the protocol object is processed by an orchestration module associated with a specific laboratory. The creation of protocol objects may occur on any computer, e.g., a user's computer, a remote computer server, or in a computer located in the laboratory. The processing of protocol objects may also occur on any computer, e.g., a user's computer, a remote computer server, or in a computer located in the laboratory.

In some embodiments, a user interface can be used in the laboratory for presenting instructions for certain steps that may need to be performed by a technician, such as retrieving a reagent from storage. Therefore, in some embodiments, the itemed list of instructions can be presented sequentially to the technician and optionally, upon completion of each instruction, the system receives a confirmation. The confirmation can be made by the technician (e.g., by scanning a barcode on the packaging of a reagent) or automatically from an instrument (e.g., the instrument sensing that a sample is loaded).

The protocol object may play a role in coordinating the design, execution and data recordation of the experiments. As provided, a protocol object is generated pursuant to the execution of an experiment function. The protocol object can then direct and coordinate the production of a new physical sample, including generating a corresponding sample object. Moreover, the protocol object may directly or indirectly interact with instruments and/or technicians to execute the experiments, monitors the process of the experiments, and record data generated from the experiments.

Execution of Experiment

Figure 18:
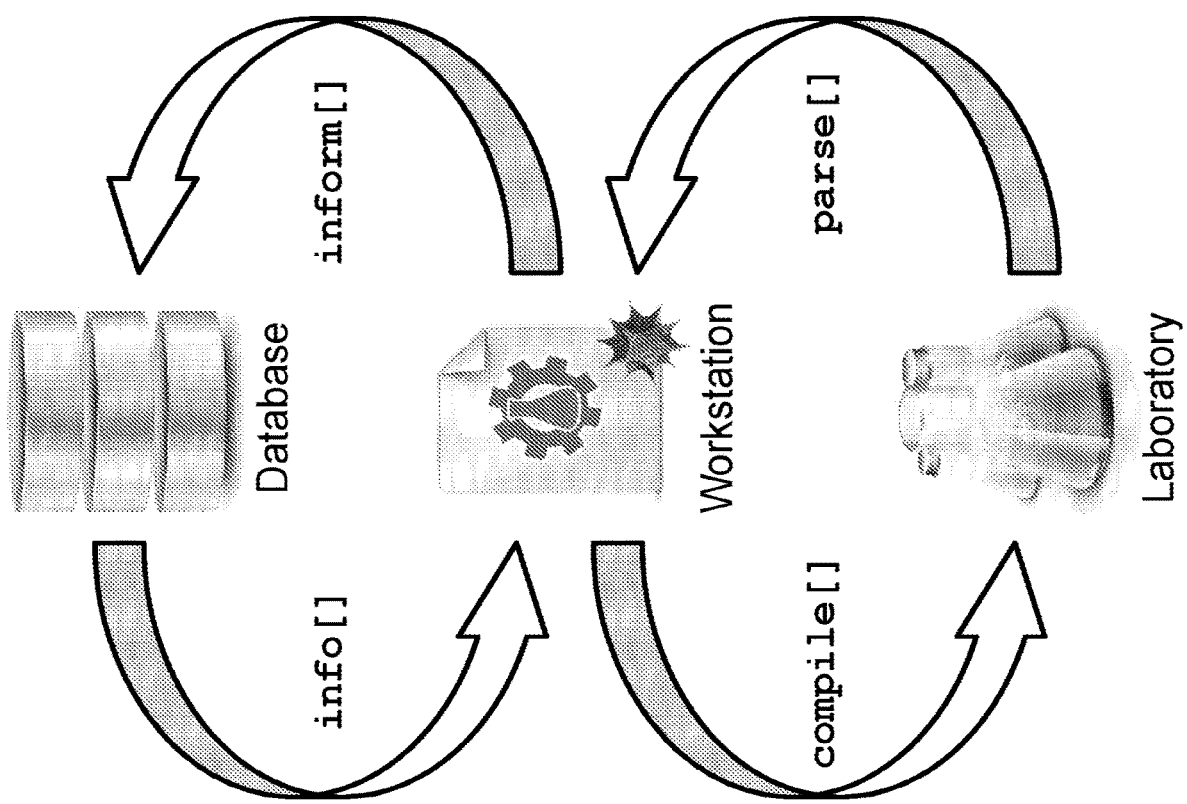
FIG. 18 illustrates an overall system design.

The system of the present disclosure can be configured according to the needs of its users. In some embodiments, the system includes one or more computers (shown as Workstation in FIG. 18) interconnected or each connected to a central server. A data source, such as a database, can be located on one of the computers, but preferably on a remote server, such as a one in a datacenter.

The system can also include one or more laboratories equipped with scientific instruments (shown as Laboratory in FIG. 18); each laboratory and its instruments are in electronic data communication with one or more of the computers in the system. In one aspect, the system includes at least one laboratory instrument for each type of experiment, e.g., synthesis, purification, amplification, quantification, cell culture, and analytics. In one aspect, the system includes at least laboratory instruments for purification, amplification, and quantification. In one aspect, the system includes at least laboratory instruments for purification, quantification, and cell culture. In one aspect, the system includes at least laboratory instruments for purification, analytics, and cell culture.

In some aspects, the laboratory instruments are configured to perform at least HPLC, PCR, and incubation. In one aspect, the system further includes a liquid handling station, flow cytometer, centrifuge, DNA synthesizer, pH meter, and microscope.

In some aspects, the system further includes various sensors for monitoring the experimental environment and HVAC (heating, ventilating, and air conditioning) systems for controlling the environment. In one aspect, the system includes at least a temperature sensor, a pressure sensor, a humidity sensor, and/or light sensor, each of which is connected to the computers of the system. In a related aspect, before, during, and/or following an experiments, sensor data are recorded in association with the experimental data for future data analysis and troubleshooting.

Program code, compilers, and parsers can be stored in one or more of the computers, which enable instruments operation, monitoring, data collection, and analysis. In some aspects, the program code configures the system to present a graphic user interface to enable a user to design experiments, monitoring experiments, and review and analyze experimental results, which are illustrated in the figures. Program code, parsers, or compilers need not be stored locally on the computer executing any aspect of the system.

Data Integration Modules

Figure 8:
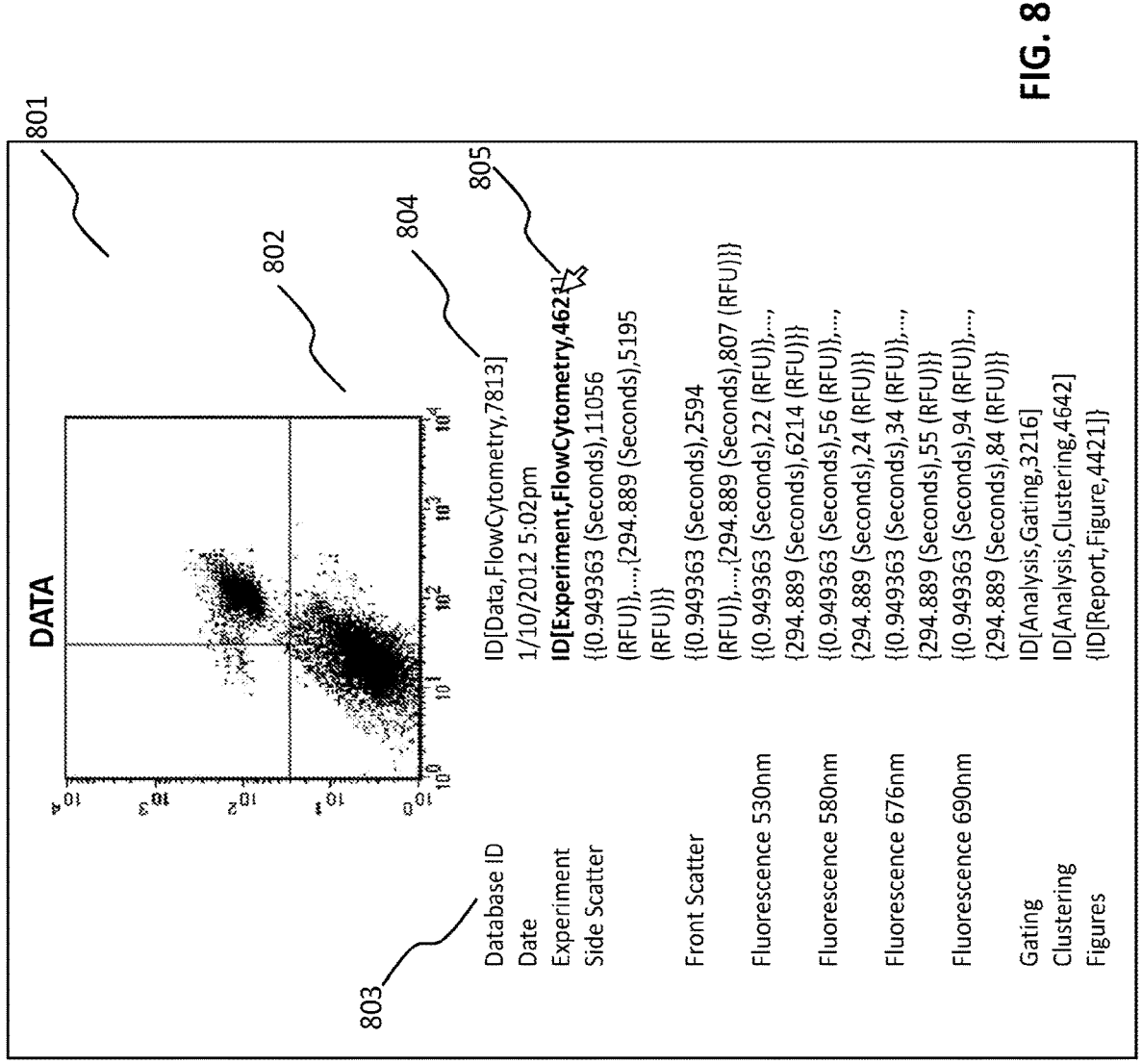
FIG. 8 shows the interface of a data module.
Figure 9:
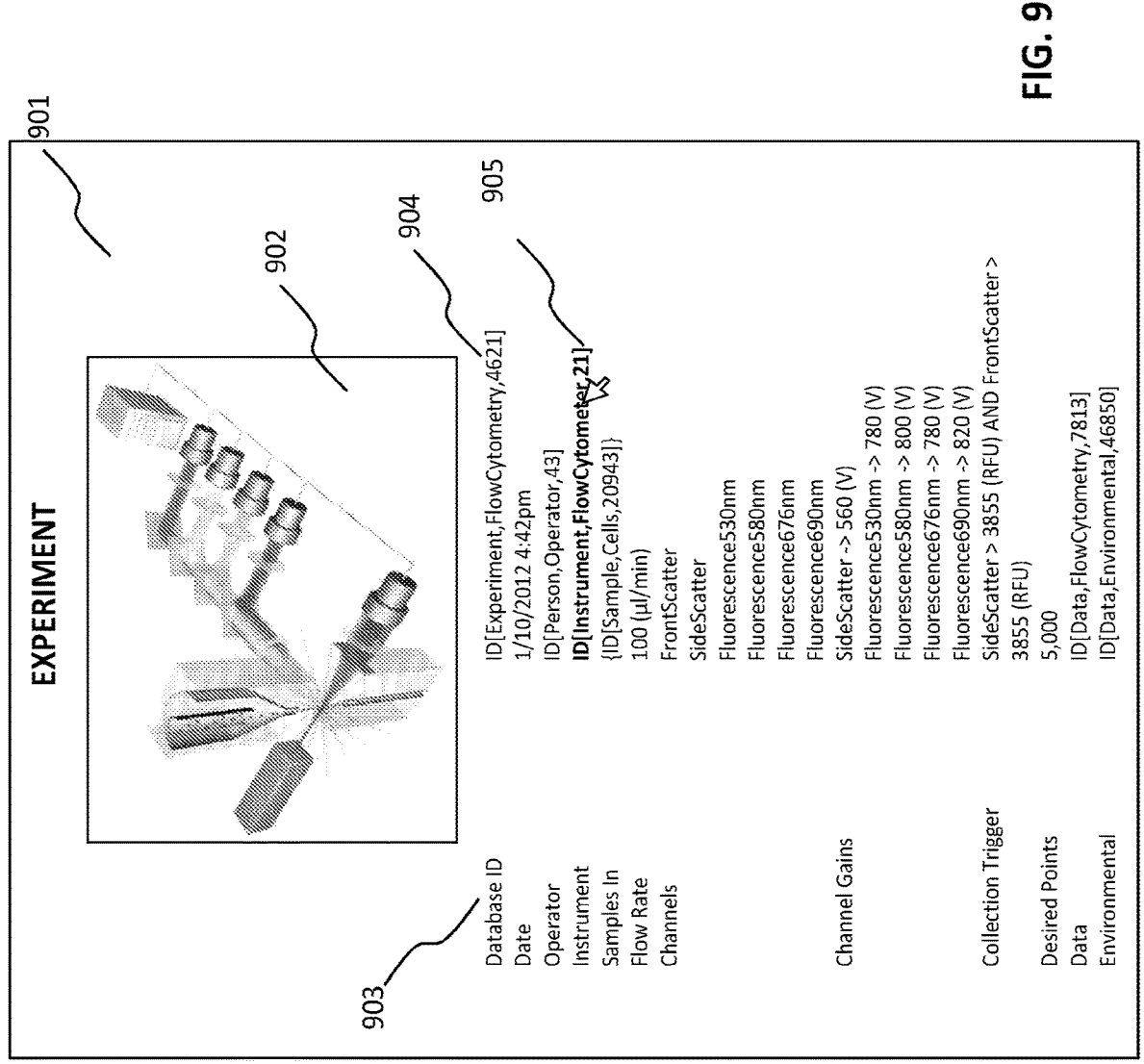
FIG. 9 shows the interface of an experiment module.
Figure 10:
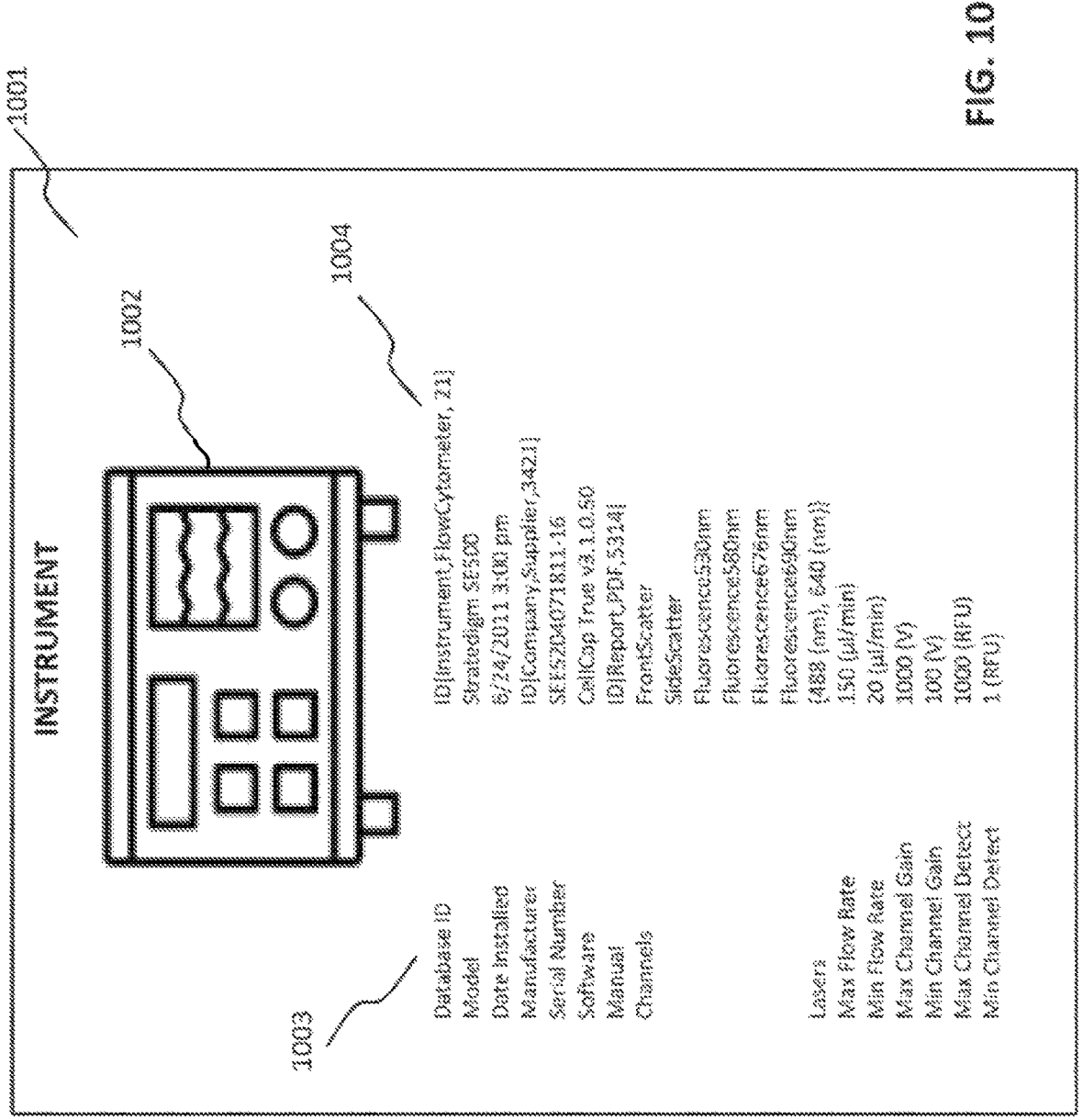
FIG. 10 shows the interface of an instrument module.

FIGS. 8-10 illustrate a few data visualization interfaces generated by the present system. Such interfaces are enabled by various objects, programs, and functions (also referred to as "modules" herein) of the SLL system. Non-limiting examples of objects and functions include "experiment," "data," "analysis," "sample," "instrument," "control," "inventory," "maintenance," "operator," "company," "model," "report," "calibration," "container," "method," "model," "part," "product," "program," "protocol," "sensor," "simulation," and "environment." In many cases a term can be associated with an object and a function, e.g., there can be both an experiment object and an experiment function.

The "experiment" module is configured to display information about an experiment. As illustrated in FIG. 9, the "experiment panel" 901 can include an optional image 902 for easy identification of the experiment type (e.g., flow cytometry). Further, the information displayed on the panel can include (column 903 represents information type and column 905 has the details):

Operator: operator of the experiment
Instrument: instrument on which the experiment was performed
Samples In: sample(s) used in the experiment
Data: data generated from the experiment
Environmental: identification of environmental record that shows measured environmental data, e.g., temperature, air pressure and humidity in the lab
Date: date and time of the experiment
Other information specific to this type of experiment, e.g., flow rates and channels.

It is noted that each of these categories of information can embed a link or other computational means leading to another module. For instance, when a user clicks the Instrument line 905, the instrument module (details below) will be invoked and present a new panel showing information about the instrument used in this experiment.

The "data" module, alternatively referred to as the "analysis" or "plot" module, is configured to display visualization of at least a portion of the data generated from an experiment on a panel (e.g., data panel 801 in FIG. 8). For any dataset, there are typically multiple ways of extracting relevant data for analysis and a variety of methods to analyze and visualize the data. The data module, in one embodiment, is configured to be able to automatically determine a suitable data extraction, analysis and visualization method, and still allow the user to adopt other available methods.

For example, recognizing that the data of FIG. 8 are taken from a flow cytometry dataset, the data module, by default, generates a scatter plot 802 at appropriate scales determined on the fly for this particular dataset. Note that this functionality is often dependent on accurate parameter resolution. For certain experimental data that are more complex, more than one data entry (e.g., shown as multiple entries on the experiment module's panel) can be generated, each leading the user to a different data analysis or visualization panel.

Similar to the experiment panel, the "data" panel includes information relating to the data (see column 803 for information type and column 804 for the detailed information):

Experiment: experiment from which the data were generated
Figures: figures generated from the instrument during experiment or from the data
Analysis: analyses available for the data
Date: date and time of the experiment
Other information specific to this type of data, e.g., gating, clustering.

Each of these categories of information can also embed a link or other computational means leading to another module. For instance, when a user clicks the Experiment line 805, the experiment module will be invoked and display information relating to the experiment.

The "analysis" module displays data analysis and related visualization, such as:

Source Data: data used in generating the analysis
Processed Data: data that have been processed for purpose of analysis
Figures: figures generated for the analysis
Date: date and time of the analysis
Other information specific to the analysis, e.g., technical details of analysis (e.g., for clustering analysis, K-means for clustering and Euclidean distance for similarity measurement)

Each of these categories of information can also embed a link or other computational means leading to another module. For instance, when a user clicks on Source Data, the system will cause the data module to display information relating to the data used for the analysis.

The "sample" module is configured to display information about a sample, which can be a sample provided by a customer received in the lab, a sample provided by a vendor, or a sample generated from an experiment. The information can include, for instance:

Supplier: person or company that provided the sample
Experiment: experiments performed on the sample
Source Experiment: the experiment from which the sample was generated
Container/Location: identification of container and/or location wherein the sample is stored
Model: the entity type of the sample and associated fields, parameters, etc. (e.g., chemical structure, protein sequence, cell type)
Control: identification of suitable control sample(s)
Date: date and time the sample was generated or received
Other information specific to a sample, e.g., type, solvent, concentration.

Each of these categories of information can also embed a link or other computational means leading to another module. For instance, when a user clicks on the Source Experiment field, the system will invoke the experiment module to display information relating to the experiment from which the sample was generated.

The "instrument" module is configured to display information about an instrument. As illustrated in FIG. 10, the information displayed on panel 1001 can include, for example, for an instrument depicted in picture 1002:

Model (see column 1003): instrument manufacturer model number (see column 1004) (not to be confused with model objects or general concept of a model in SLL)

Experiments: listing of experiments that have been run on the instrument

Maintenance: listing of maintenance performed for the instrument

Controls: control experiments/samples run on the instrument

Data: data sets generated from experiments run on the instrument

Date of Installation: date and time of instrument installation

Visualization: pictures of the instrument

Manual: manual document

Other information specific to an instrument, e.g., serial number, software.

Each of these categories of information can also embed a link or other computational means leading to another module. For instance, when a user clicks an experiment listed under Experiments, the system will invoke the experiment module to display information relating to the experiment run on the instrument. Because of the linked nature of the objects it is easy to run highly flexible and unique queries like see all the samples that came out of the experiment (protocol[123,Western][SamplesIn] or, equivalently, SamplesIn/.Info[protocol[123,Western]]) or see all the peak picking analyses that were performed on the Western data mass spectrums (protocol[123,Western][Data][PeaksSourceSpectra] or, equivalently, PeaksSourceSpectra/.Info[Data/.Info[protocol[123,Western]]])

The "control" module is configured to display information about a control experiment conducted with one or more sample on an instrument for calibration and/or quality control purpose. In some embodiments the control module is the experiment module displaying control experiments. A control module can present information that include, for example:

Sample: sample used for conducting the control experiment

Instrument: instrument for which the control experiment was run

Result: indicates whether the control experiment passed or failed

Data: data generated from the control experiment

Expected Values: expected values or value ranges for certain data point in a result Visualization: data visualization from the data Date: date and time when the control experiment was run Other information specific to a control experiment, e.g., control type.

Each of these categories of information can also embed a link or other computational means leading to another module. For instance, when a user clicks on the instrument, the system will invoke the instrument module to display information relating to the instrument.

The "inventory" module is configured to display information about an inventory of samples, experiment, and/or data for a user of a group of users (e.g., a company). An inventory module can present information that include, for example:

Samples: listing of samples provided by or generated for a user or user group

Experiments: listing of experiments designed by or run for a user or user group

Data: data generated from the listed experiments

User: user or user group (e.g., company)

Other information specific to an inventory, e.g., last edit time.

Each of these categories of information can also embed a link or other computational means leading to another module. For instance, when a user clicks on a sample, the system will invoke the sample module to display information relating to the sample.

The "environment" module, sometimes also called the "sensor" module, is configured to display environmental information collected when an experiment was conducted. It is understood that environmental factors such as temperature and air pressure in the laboratory could have impact on an experiment. Nevertheless, likely due to a lack of a suitably integrated system or recognition of the significance of these factors, such environmental factors are often not considered when designing, conducting, and recording experiments. In the present technology, environmental variables are tightly controlled and their details are recorded for post-experiment analysis. Non-limiting examples of environmental factors include temperature, air pressure, humanity, brightness, and air purity (e.g., PM2.5). An environment module, in accordance with one embodiment of the disclosure, is configured to display measurements for any one or more of the environmental factors, and associates them to the experiment being conducted. Factors may be of a general or local nature, e.g., temperature in the laboratory versus temperature in the vicinity of a specific liquid handler.

Without limitation, the present system also includes the following modules, a "maintenance" module for displaying maintenance information for an instrument, a "model" module for displaying entity information for a particular sample (e.g., chemical structure for a chemical sample, protein sequence for a protein sample, cell type for a cell sample), a "report" module for displaying collective information relating to any matter in the system, such as literature relating to a model, an "operator" module for displaying information of an operator that conducts an experiment (e.g., loading a sample to the system), and a "company" module for displaying information about a company (e.g., vendor of an instrument).

Data Exploration and Visualization

The integrated laboratory system and data integration modules enable a user to explore any data associated with an experiment collected by the system in a user-friendly fashion. A few examples are illustrated in FIGS. 14-17. The following examples are presented in manner that requires interaction with a user through a graphical user interface. On the graphical user interface, the user can view certain displayed information of a module, and interact with the system by clicking on a link or through other input mechanisms. However, such examples are for the purpose of illustration only, as it would be readily appreciated by one of skill in the art that exploration of data in a system does not necessarily require visualization, much less graphical visualization. Further, navigation through different modules also does not require a mechanical action by a user and can be carried out merely with machine-readable code or instructions. Therefore, a click in the examples below can be understood as invoking a function or executing a command.

Figure 14:
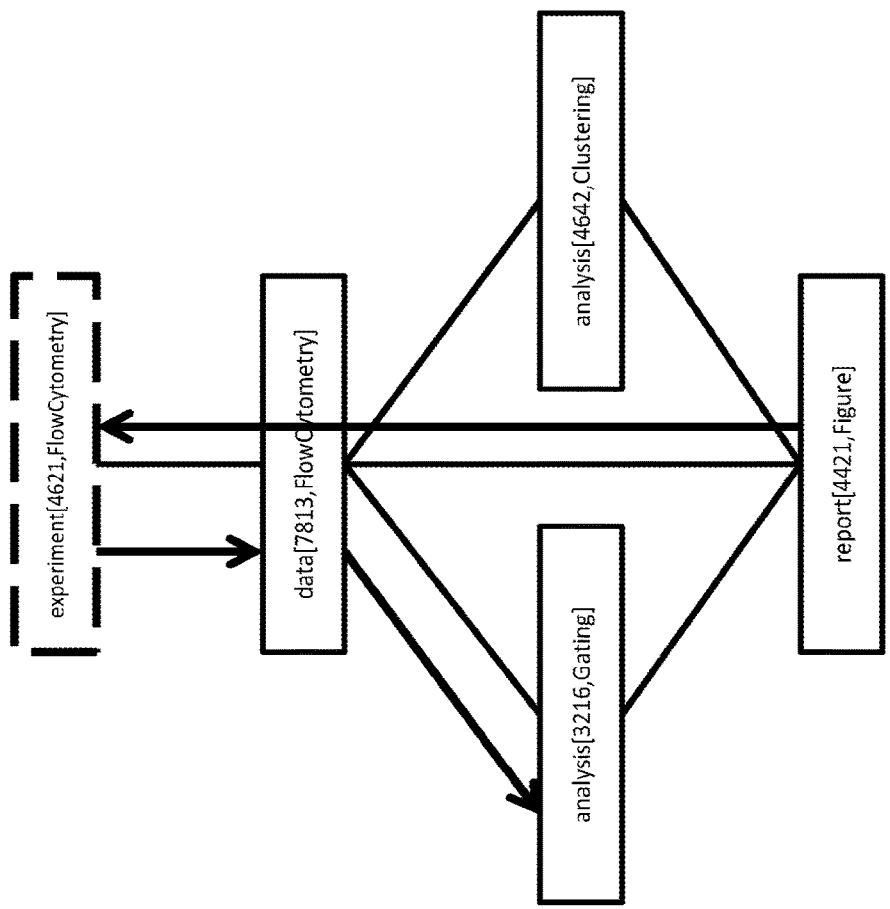
FIGS. 14-17 show a few examples of interconnected objects generated or utilized for data exploration and mining.

In FIG. 14, when a user opens a panel with a command (e.g., by clicking or entering the appropriate script) to invoke the experiment module for a project, the experiment module displays on the panel information relating to the experiment in the project. In this instance, the experiment is a flow cytometry experiment (top box, see also FIG. 9). On the panel, the user can click on a link embedded in the text indicating data generated from the experiment (see second to last line on FIG. 9), and the data module is invoked, displaying a new panel (data panel, see also FIG. 8).

The data panel displayed by the data module shows, in addition to the text information links in columns 803 and 804, an optional FIG. 802. The figure does not need to represent all data generated from an experiment. Further, in some aspects, as the figure provides an overview of the data, its generation does not require user input. Therefore, in some aspects, the system automatically chooses data extraction/transformation and visualization technique to present the data. For instance, for flow cytometry data, the data module automatically chooses a scatter plot and scales that accommodate at least 95% of the available data points.

Like the experiment panel, the data panel also includes links to other modules/panels. The link 805, for example, points the user back to the experiment panel.

As a dataset can be analyzed with multiple methods, the data panel can also include links to multiple instances of the analysis module (shown as two analysis module blocks in FIG. 14). Here, one analysis is for gating and the other for clustering. When invoked, the analysis module can display source data, method's details of the analysis, and analysis results, without limitation.

In addition to generating an analysis panel with no or minimum user input, from a dataset generated from an experiment, the system can also create a report from the analysis results. From the outside, when a user clicks on a report link on either of the analysis panel, the report module will bring up a panel showing the report.

In one aspect, the report panel displays a collection of information relating to the experiment. Like the analysis panel and unlike conventional reports, the report panel here can be dynamic as it is supported by an integrated data source and connected to the laboratory instruments.

Figure 12A:
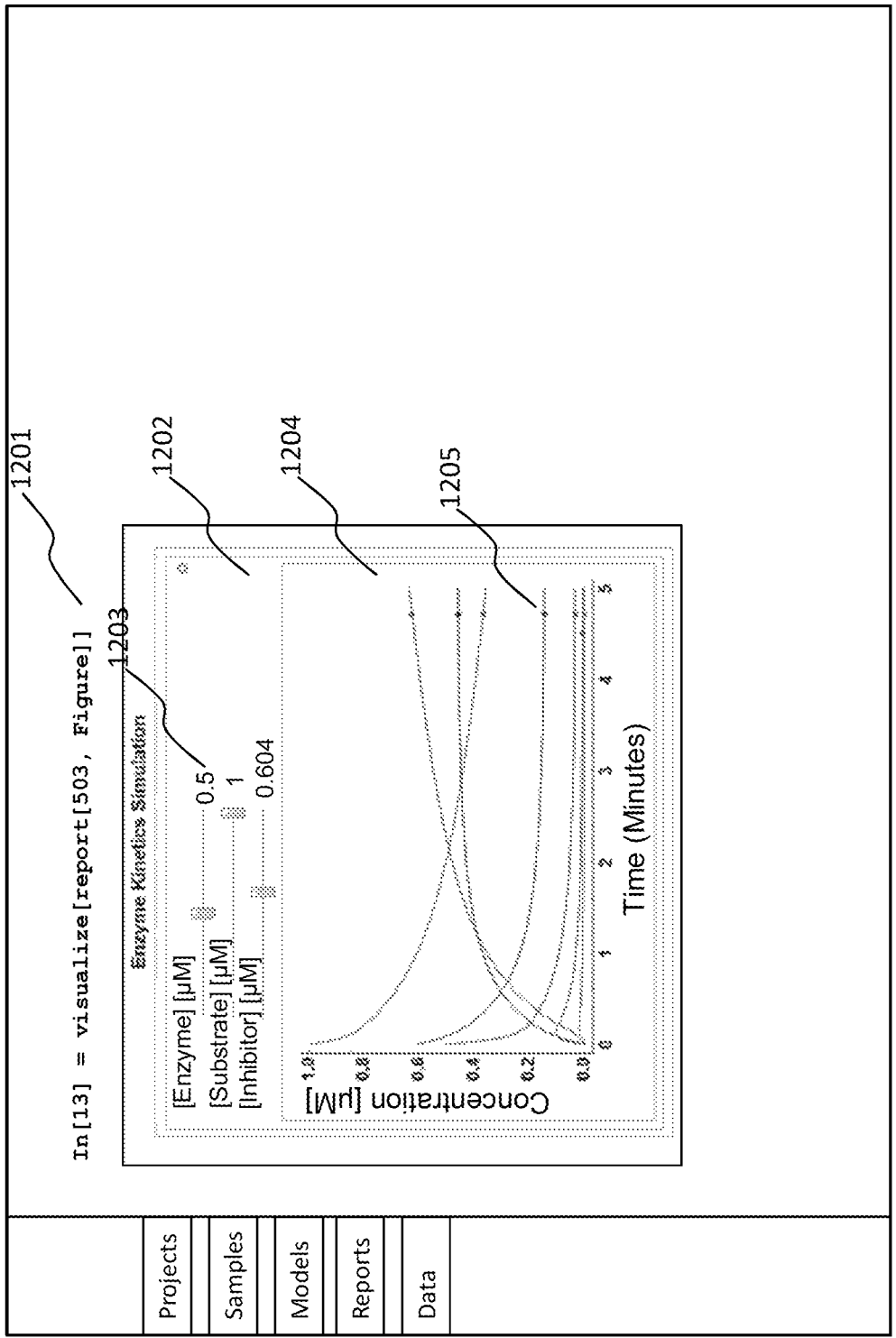
FIGS. 12A-C show a visualization panel that can be included on the interface of an analysis or report module with a variety of plots.

For instance, FIG. 12A shows a dynamic figure that can be included in the analysis and report panels. Here, the time-dependent concentration curves (1204) are presented for an enzyme kinetics simulation, which can be used for comparing to an actual experiment. On top of the curves, there are three moveable bars (1203) allowing the user to change and see instant simulation results from the changes. Even on the curves, if the user moves the cursor to a particular point (e.g., 1205), the user will be able to tweak the curves to fit a need. It can also be seen that the script 1201 is used to generate the visualization and any change to the script can lead to update or re-creation of the visualization.

Figure 15:
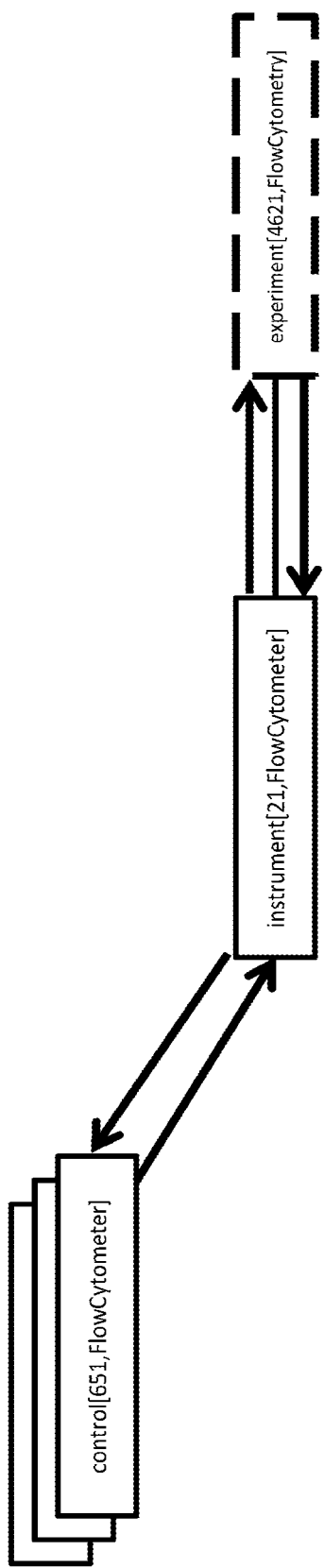

FIG. 15 illustrates another case in which a user can click through an experiment panel to examine the instrument used in the experiment, and then control experiments conducted on the instrument. The control example can be a most recent control experiment before the actual experiment was performed, or one that was run closest to the actual experiment (including afterward). In some aspects, the control experiment is the same in kind as the actual experiment if the instrument is able to handle different types of samples and experiments.

Figure 16:
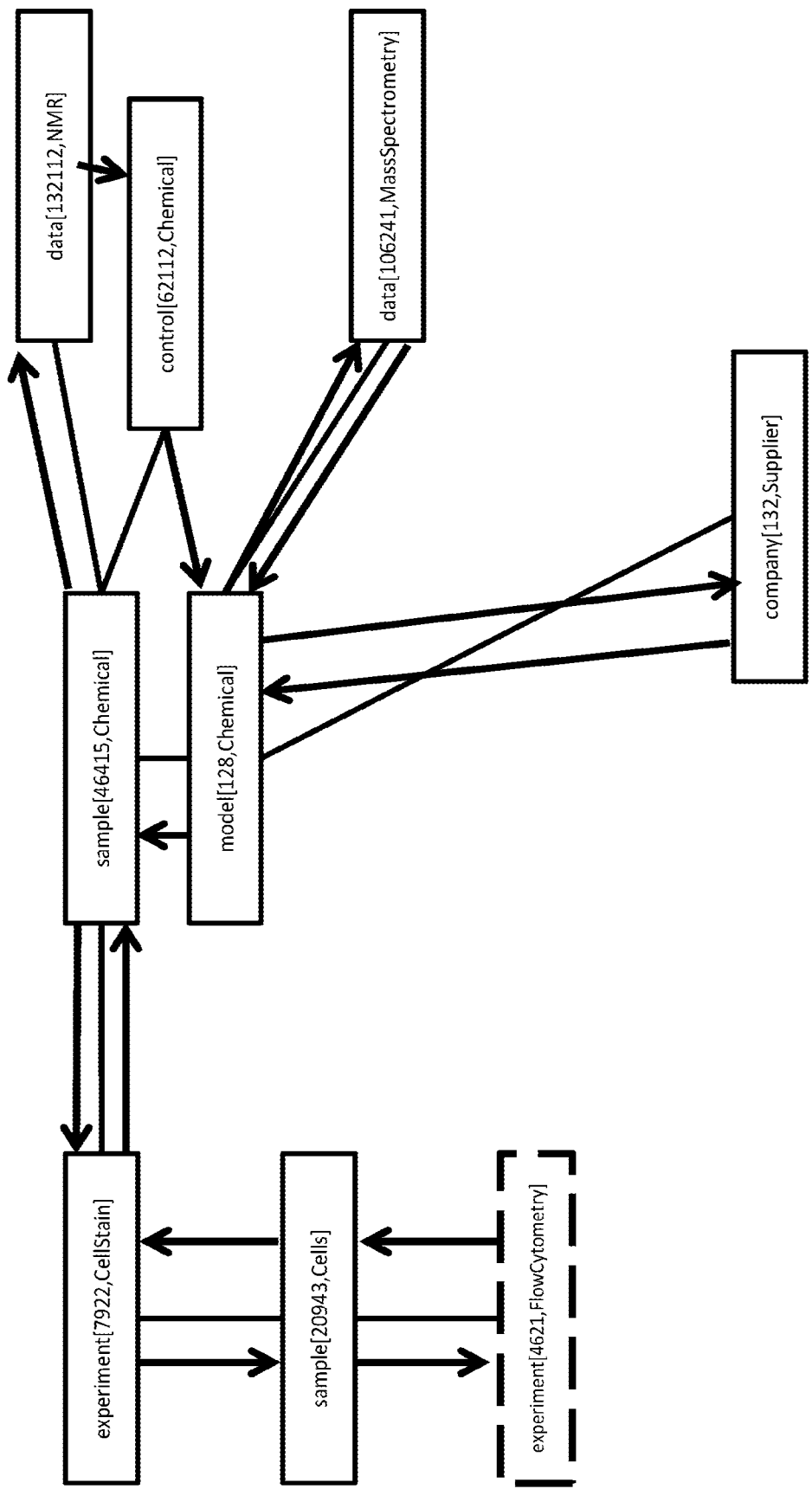

In FIG. 16, when a user clicks on a link to the sample (a cell sample) used in the experiment (flow cytometry), the user can then check out another experiment (cell staining) conducted on the sample. Then, through a panel displaying the staining experiment, the user can view a different sample (e.g., a chemical sample) used for the staining. Through the sample panel, the user can in turn access a model panel showing chemical structure, vendor (again to access the vendor information on the company panel), and other information relating to the chemical entity of the chemical sample (e.g., mass spectrometry data available to the chemical entity). In addition, from the chemical sample panel and the model panel respectively, the user to click on data and control links to view the NMR data of the chemical and relevant control samples for this chemical entity.

Figure 17:
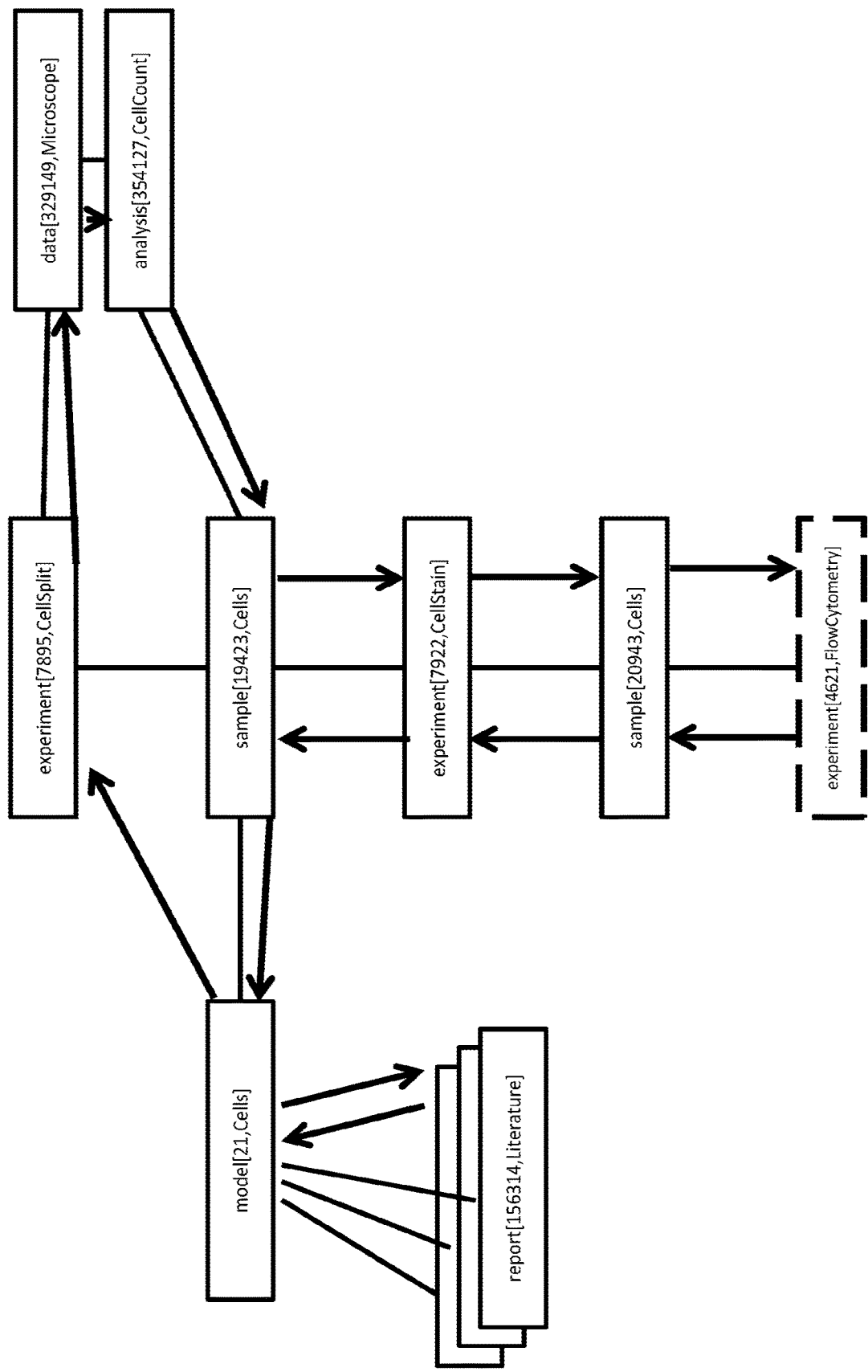

While the example in FIG. 16 highlights the system's ability to associate different experiments though a common sample, the example in FIG. 17 shows the system's ability to conduct a compound experiment.

In FIG. 17, a cell sample 20943 is run in a flow cytometry experiment. The collected cells after the flow cytometry experiment is then subject to a cell staining experiment, which identifies certain cells (19423) as output. These output cells are then run in a cell split experiment, which generates data and analysis of the data. The identified sample is intended to be of a particular type (model 21). If a user is interested in learning more about the cell type, the user can find literature information by clicking on the report link on the model panel.

Figure 11:
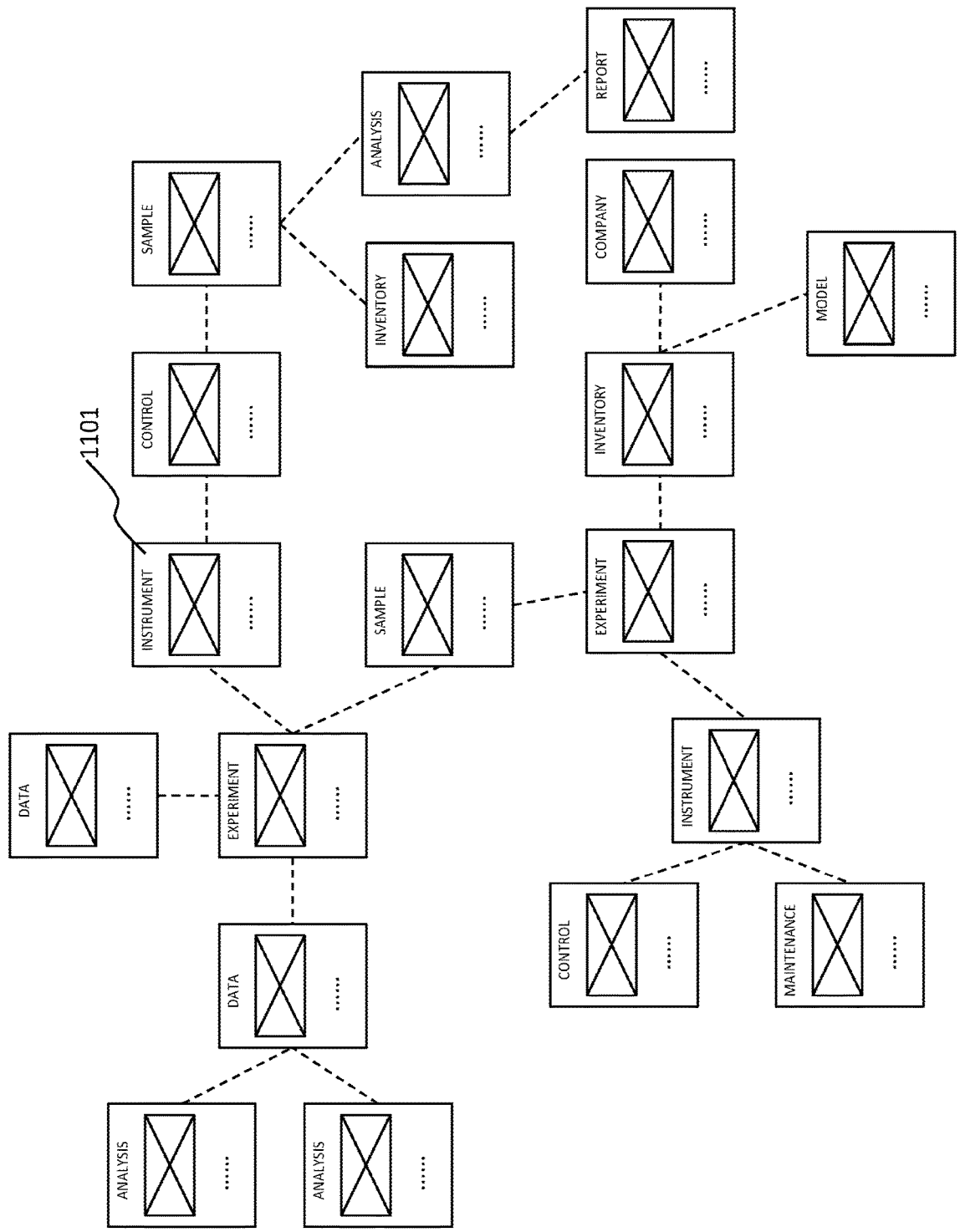
FIG. 11 shows an example in which a number of objects are interconnected through links on their interfaces, allowing a user to explore relevant information.
Figure 13:
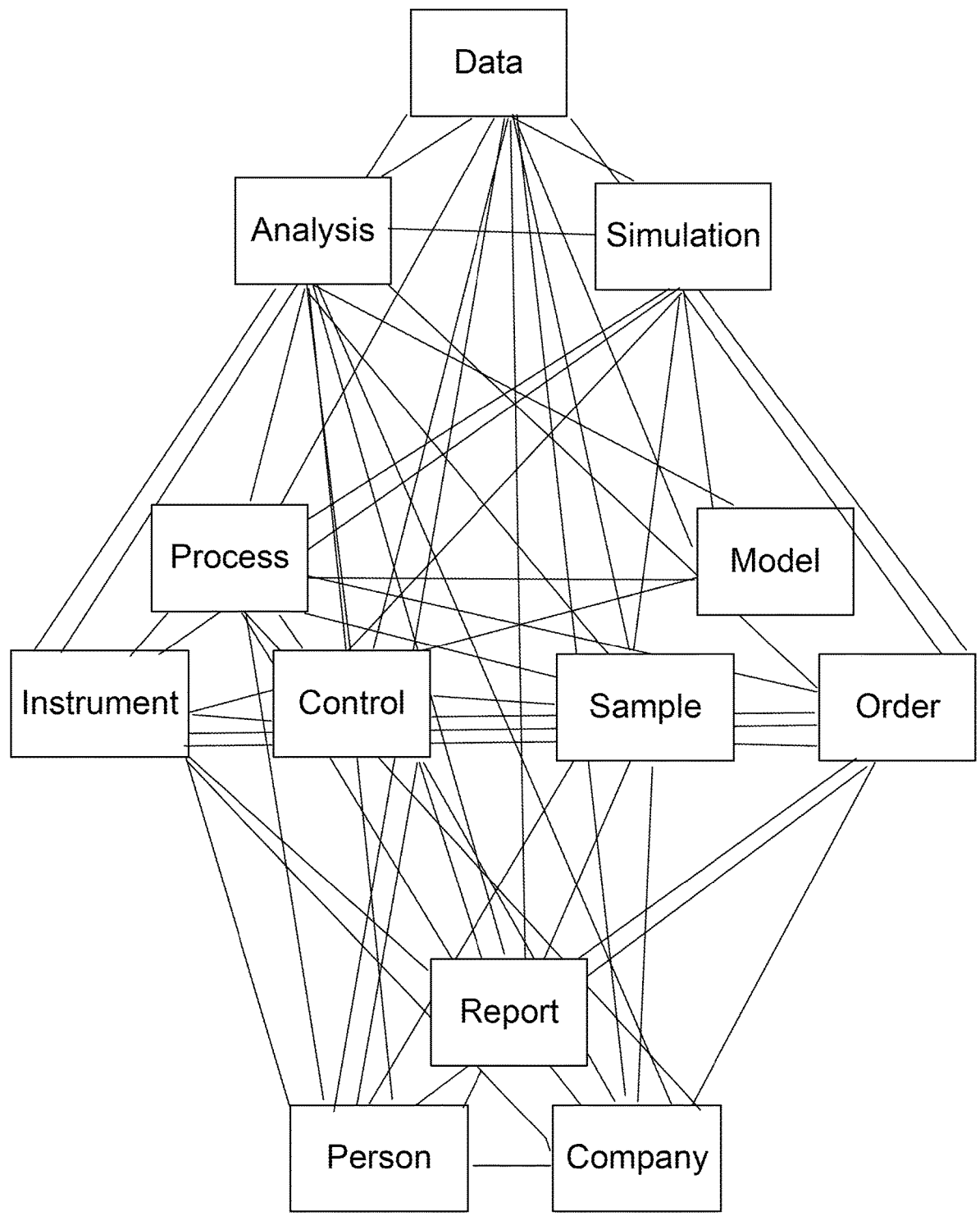
FIG. 13 illustrates how the system integrates different element of a laboratory research project which can be performed on the system.

All these capabilities and others are partially represented in FIG. 11, with each dotted line representing linkage allowing users to navigate between the connected panels through links presented on their interfaces. The interconnectivity of the system can be summarized in FIG. 13.

Figure 12B:
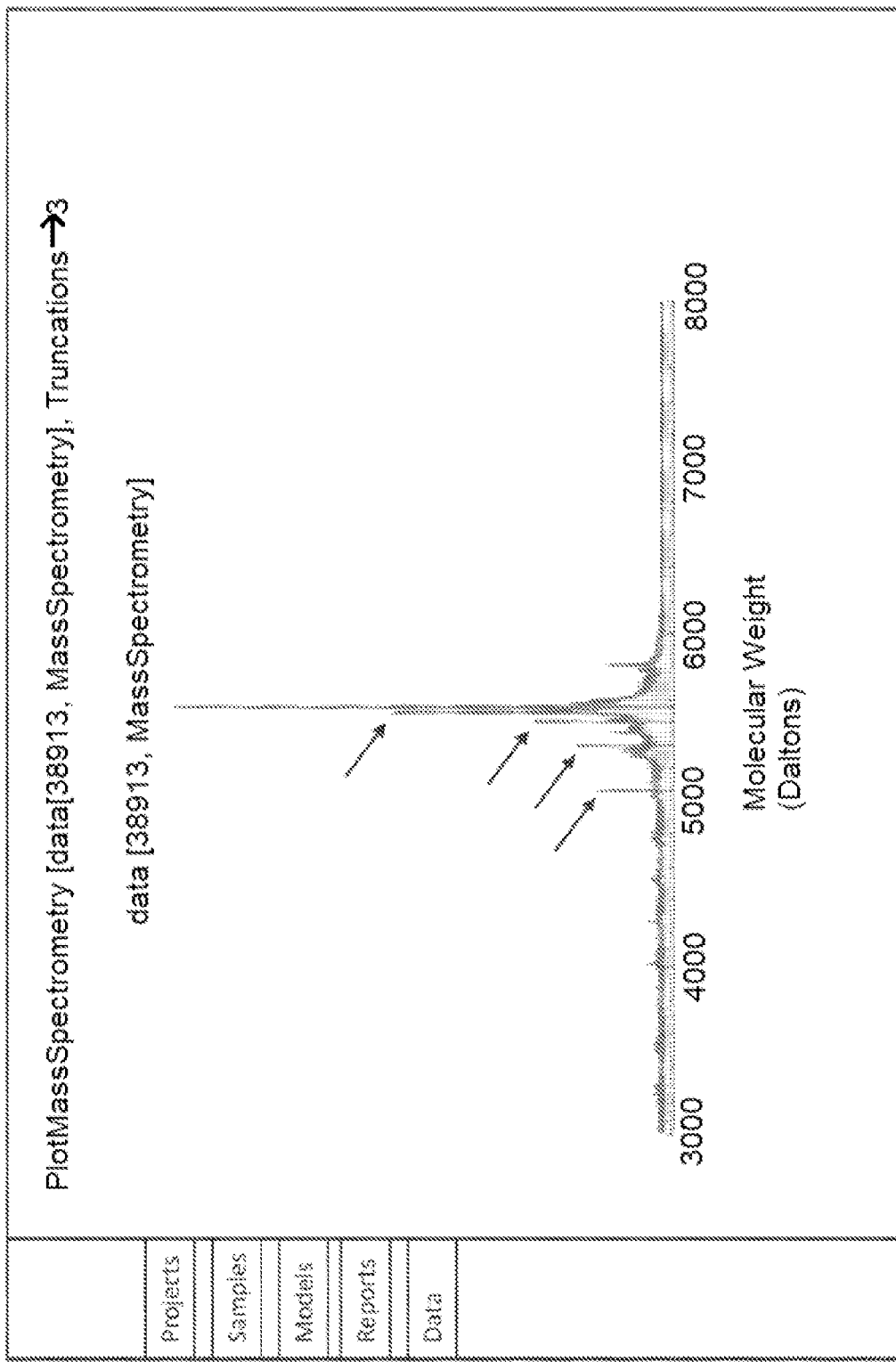
Figure 12C:
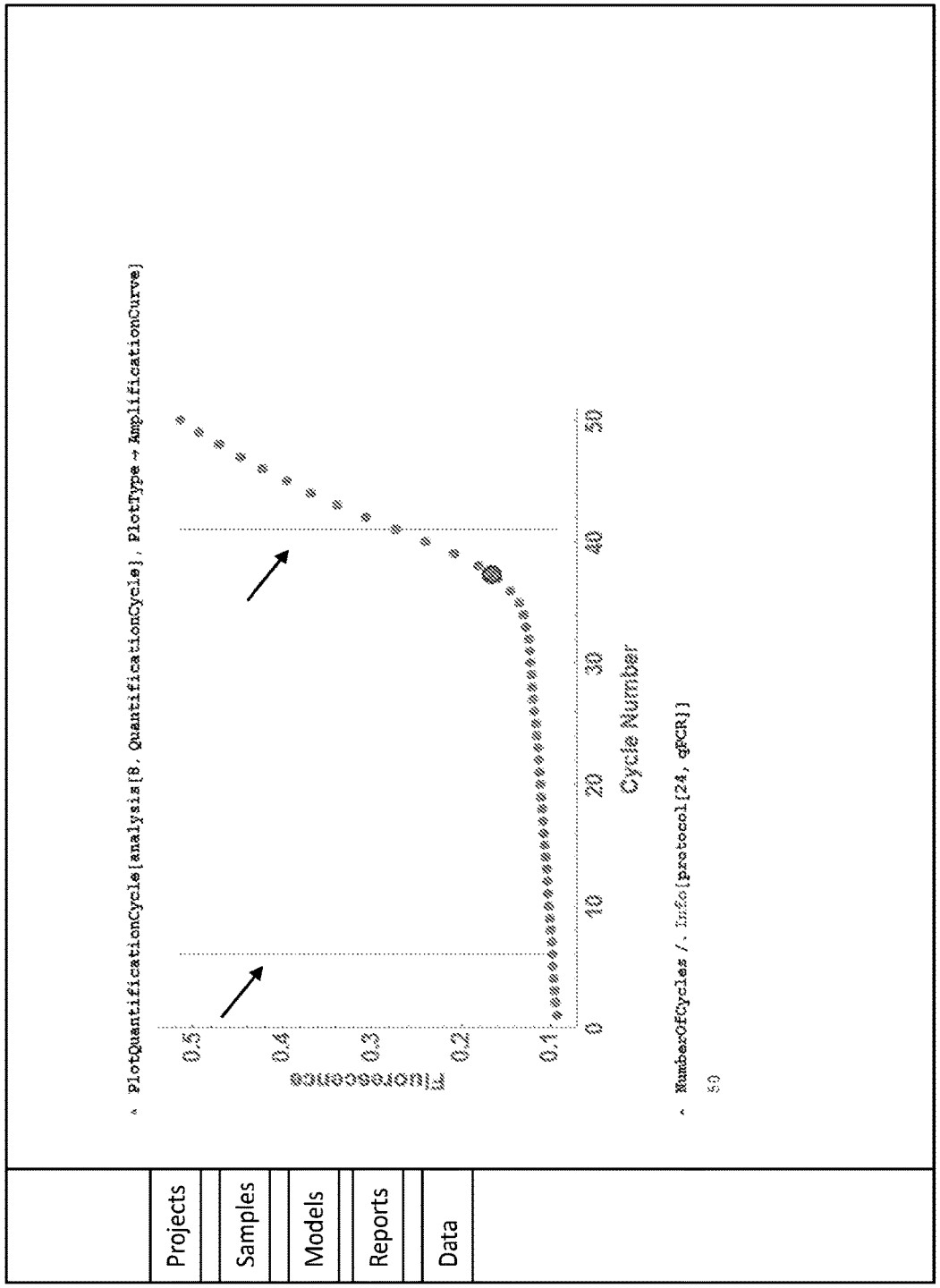

FIGS. 12B and 12C show two plots which illustrate an advantage of the present technology over the conventional art. In the plot PlotMassSpectrometry of FIG. 12B, the straight vertical lines (indicated by arrows) indicate where system estimates the peaks should be. This is only possible with the integration of experiment design, execution and analysis. The PlotMassSpectrometry function accesses the data object that contains the raw mass spec data that goes into the plot, dereferences the link to the sample object associated with that data object, then dereferences the link to the model object associated with the sample (the model includes the putative nucleic acid sequence of the sample), then calculates the molecular weight of the sample based upon the information in the model object, as well as calculate the molecular weight of n-1, n-2, and n-3 truncated versions of the sample. For example, if the model indicates the sample is ATGCATATGC, then it calculates the molecular weight for: ATGCATATGC, ATGCATATG, ATGCATAT, and ATGCATA. This is helpful since one would expect a synthesis process to sometimes terminate early, and therefore the sample ought to have peaks corresponding to those shorter strands. For purposes of visualization, the PlotMassSpectrometry function then centers the graph around the calculated expected molecular weight of the sample. Such integration is also advantageous if, for example, someone views this plot years from now and wishes to view the underlying sequence of the sample assayed and then resynthesize the same sample for use in his own experiments. That is somewhere between very difficult and impossible in the art, but is borderline trivial to execute with the disclosed invention; it could be accomplished with a single line of scripting, e.g., data[38913,MassSpectrometry][SamplesIn] [Model][Strand] or, equivalently, Strand/.Info[Model/.Info [SamplesIn/.Info[data[38913,MassSpectrometry]]]] retrieves the sequences, which can then be inputted into a new synthesis experiment.

Such an advantage arises from one embodiment of the presently disclosed system that is tightly integrated and the analysis functions are capable of tracing data all the way back to the functions that set up the experiment that generated the data and interrogating the experiment settings. The parameter checking up front on the experiment function side in the user interface ensures that when the experiment is set up that all the necessary information is specified. Such integration can be helpful in ensuring experiment execution and, in addition, ensuring analysis of the resulting data and leveraging such guarantee to support a more powerful analysis experience.

Another example that highlights the advantage of integration is a PlotQuantificationCycle plot shown in FIG. 12C. There, to determine the upper bound of the visualization, the plotting function accesses the experiment protocol, pulls number of cycles specified for the experiment, and then sets the upper limit and lower limit (indicated by arrows) based on actual number of cycles performed. The rest of the data can be considered spurious since the function knows that only n number of cycles were run. Discarding the spurious data improves the automatic calculation of the appropriate inflection point (circle).

Accordingly, in one embodiment, a data analytic method of the present disclosure entails including, in the analysis of an experiment (the present experiment), reference data that are not directly generated from the present experiment. One example of such reference data may be values of the experimental parameters that were either provided by a user, computed by the system with input from a user, or computed by the system without using any input from a user. Another example of such reference data may be information about the instrument, such as the calibration method of the instrument.

Yet another example of such reference data may be environmental conditions under which the present experiment was run, including but not limited to temperature, brightness, and humidity. Also of importance, in yet another example, the reference data are derived from any information concerning an experiment that precedes the present experiment and is preferably associated with the present experiment. Such a preceding experiment can be one that produces a sample used in the present experiment, that analyzes a sample of the present experiment, or that reveals a condition of the present experiment. In some embodiments, the reference data impose a limitation on the interpretation of the present experiment, are used to clean up the result of the present experiment (e.g., eliminate irrelevant, invalid, or less important portion of the data), or serve as standard or control for the present experiment. In some embodiments, the data from the preceding experiment are used to interpret the result of the present experiment.

Figure 19:
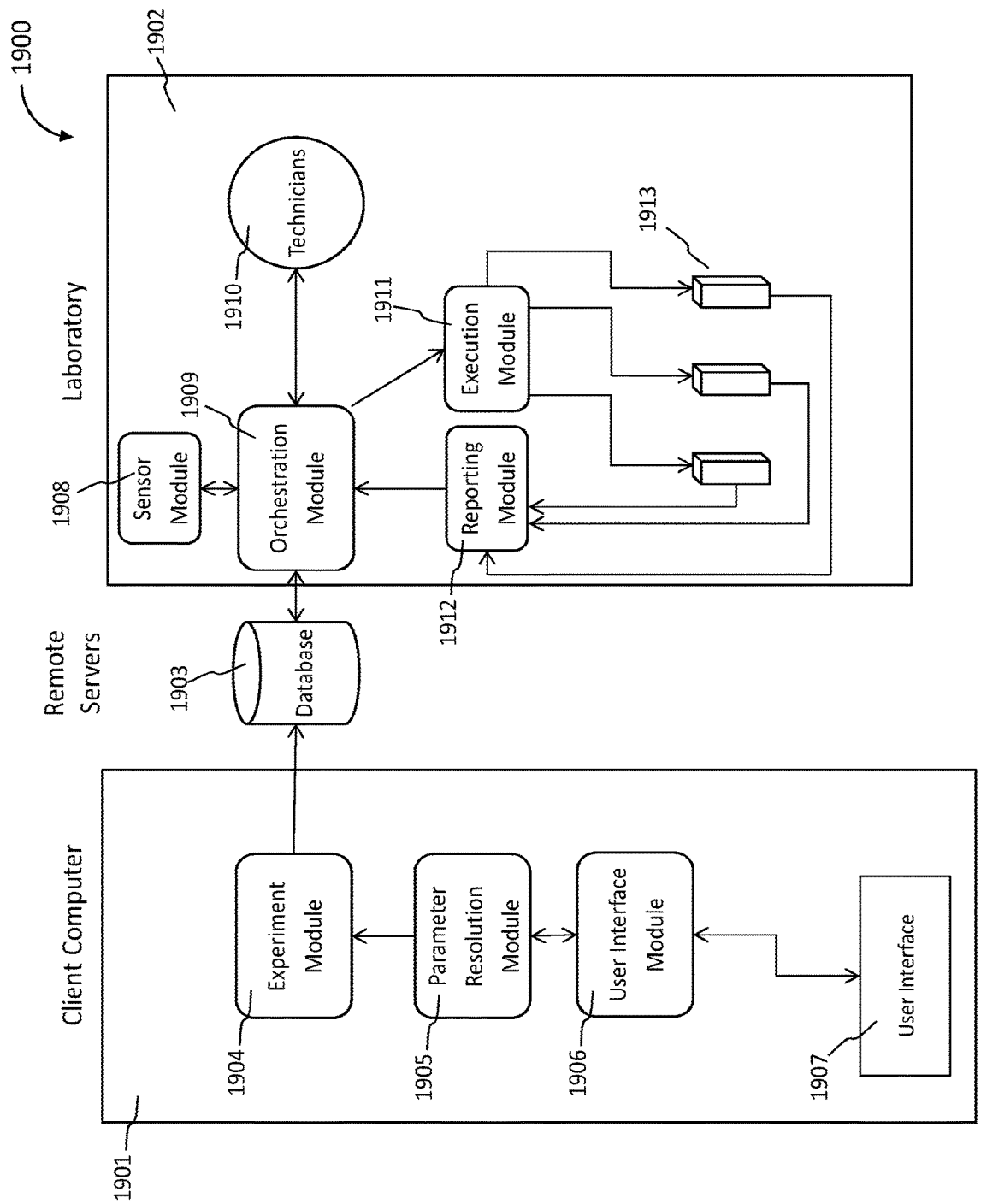
FIG. 19 illustrates a system of one embodiment of the present disclosure.

In one embodiment, the present disclosure provides a system for developing scientific experiments. The system can include memory, processors, instruments, and certain software environment and modules. As illustrated in FIG. 19, the system 1900 can conceptually be divided into two portions, with some modules located on a client computer (1901) where some can be considered more directly relevant to the laboratory setting (1902). They can be connected through a database (1903) on a remote server. As readily appreciated by one of skill in the art, the configuration illustrated in FIG. 19 is for illustration only and does not limit how the system can be configured.

In one embodiment, the system includes an experiment module (1904), a parameter resolution module (1905), and a user interface module (1906). In some embodiments, two or more experiment modules are included in a software-based development environment of the system, each of which comprises one or more parameters and one or more criteria for each parameter, and is configured to generate instructions for carrying out an experiment technique with the one or more parameters.

The experiment module 1904 is in communication with a user interface module 1906 which can present a user interface (1907) on which the system can receive, from a user, commands to execute two or more experiment techniques. Each command can include input value for one or more parameters for one of the experiment techniques. These input values can be referenced in the parameter resolution module (1905) for parameter resolution. There, for instance, for each parameter for which an input value is received, the parameter resolution module determines whether the input value is valid based upon at least one of the criteria for the parameter. Such determination can also take information from the experiment module. Further, for each parameter for which an input value is not received but can be computed, the parameter resolution module computes a value based upon at least one of the criteria for the parameter. Subsequently, the parameter resolution module can generate a warning if at least one parameter lacks an input value.

Upon parameter resolution, an experiment or, in certain embodiments, two or more experiment techniques can be saved and executed. The information can be saved in a database (1903) where the information can be retrieved by other portions of the system. Execution of the experiment can be coordinated by an orchestration module (1909), which interacts with technicians (1910) for carrying out (and confirming) certain steps (e.g., locating a sample) of the experiment. The orchestration module can also instruct the sensor module (1908) to monitor various experimental conditions and environmental conditions. Execution of the experiment can be controlled by an execution module (1911) that makes calls to various instruments (1913) in the laboratory, which send data or report to the reporting module (1912). Each of these modules can interact with the orchestration module directly or indirectly.

The system as illustrated in FIG. 19 can be adapted to execute two or more experiment techniques, or alternatively three or more, four or more or five or more experiment techniques. In some embodiments, the experiment techniques selected from the group consisting of Analytical Balance Readings, Apoptosis Assays, Autoclaving, Buffer Prep, Centrifugation, DNA/RNA Synthesis, Epifluorescence Microscopy, Fast Protein Liquid Chromatography (FPLC), Flash Chromatography, Flow Cytometry, Fluorescence Kinetics, Fluorescence Polarization, Fluorescence Spectroscopy, Fluorescence Thermodynamics, Genomic DNA Prep, HPLC (Ion Exchange), HPLC (Reverse Phase), Light Microscopy, Liquid Handling, Lyophilization, MALDI Mass Spectroscopy, Mammalian Cell Culture, pH Readings, Polyacrylamide Gel Electrophoresis (PAGE), Polymerase Chain Reaction (PCR), Protein Extraction, Quantitative Real Time PCR (qPCR), RNA Extraction/cDNA Prep, Rotary Evaporation, Solid Phase Extraction, Speedvac Concentration, Thermometer Readings, Thin Layer Chromatography (TLC), Total Protein Quantification, Transfection, UV/Vis Kinetics, UV/Vis Spectroscopy, UV/Vis Thermodynamics, Vacuum Filtration, Viral Prep, Volume Check, Western Blot, Agarose Gel Electrophoresis, *Arabidopsis* Studies, Atomic Absorption Spectroscopy, Atomic Emission Spectroscopy, Atomic Force Microscopy, Bacterial Cell Culture, Bio-Reactor, Bomb calorimetry, *C. elegans* Studies, Capillary Electrophoresis, Circular Dichroism (CD), Colony Picking, Confocal Microscopy, Crossflow Filtration (TFF), Crystallization, Dialysis (Equilibrium), Dialysis (Preparative), Differential Scanning calorimetry (DSC), Digital Droplet PCR, DNA Sequencing (Next Generation), DNA Sequencing (Sanger), *Drosophila* Studies, Dynamic Light Scattering (DLS), Electron Microscopy, Electroporation, Electrospray Ionization (ESI) Mass Spectrometry, Enzyme-Linked Immunosorbent Assay (ELISA), Flow Chemistry, Fluorescence Activated Cell Sorting (FACS), Fluorescence In Situ Hybridization (FISH), Gas Chromatography, Gas Chromatography Mass Spectrometry (GC-MS), HPLC (Normal Phase), HPLC (Preparative), Immunoprecipitation, Inductively Coupled Plasma Mass Spectrometry (ICP-MS), Infrared Spectroscopy, Isothermal Titration calorimetry (ITC), Liquid Chromatography Mass Spectrometry (LC-MS), Liquid-Liquid Extraction, Melting Point Determination, Microarray Analysis, Microwave Reactions, Molecular Cloning, NMR (2D/Structural), NMR (Carbon), NMR (Proton), Organic Synthesis (Milligram to Gram Scale), Patch Clamp Recordings, Peptide Synthesis, Photostimulated Luminescence (PSL), Plasmid Construction, Refractometry, Scanning Tunneling Microscopy, Solubility Testing, Sonication, Supercritical Fluid Chromatography (SFC), Surface Plasmon Resonance (SPR), Tandem Mass Spectrometry (MS-MS), Tissue Homogenization, Total Internal Reflection Fluorescence (TIRF) Microscopy, Ultracentrifugation, X-Ray Crystallography, and Yeast Cell Culture.

In some embodiments, one of the conditions is that no warnings are generated. In some embodiments, one of the conditions is that only non-critical warnings are generated.

In some embodiments, the execution module is further configured to generate an object reflecting the received commands. In some embodiments, the execution module is further configured to utilize the generated object in a physical laboratory to perform the experiment techniques specified by the received commands.

In some embodiments, the system further comprises a module for receiving data generated by the execution of the received commands. In some embodiments, the system further comprises a module for displaying a portion of the received data in the software-based development environment. In some embodiments, the system further comprises a module for analyzing a portion of the received data in the software-based development environment. In some embodiments, the system further comprises a module for generating a graphical element based upon the analysis of the received data. In some embodiments, the system further comprises a module for receiving one or more additional executable commands from the user after receiving the data.

In some embodiments, the software-based development environment includes graphical elements for selecting executable commands. In some embodiments, the software-based development environment includes functionality for graphical display of received data.

Another embodiment of the present disclosure provides a system for analyzing data obtained from a laboratory experiment. The system may include a processor, memory, and program code that includes one or more modules as describe below. Some example systems are illustrated in FIG. 20A-G.

Figure 20A:
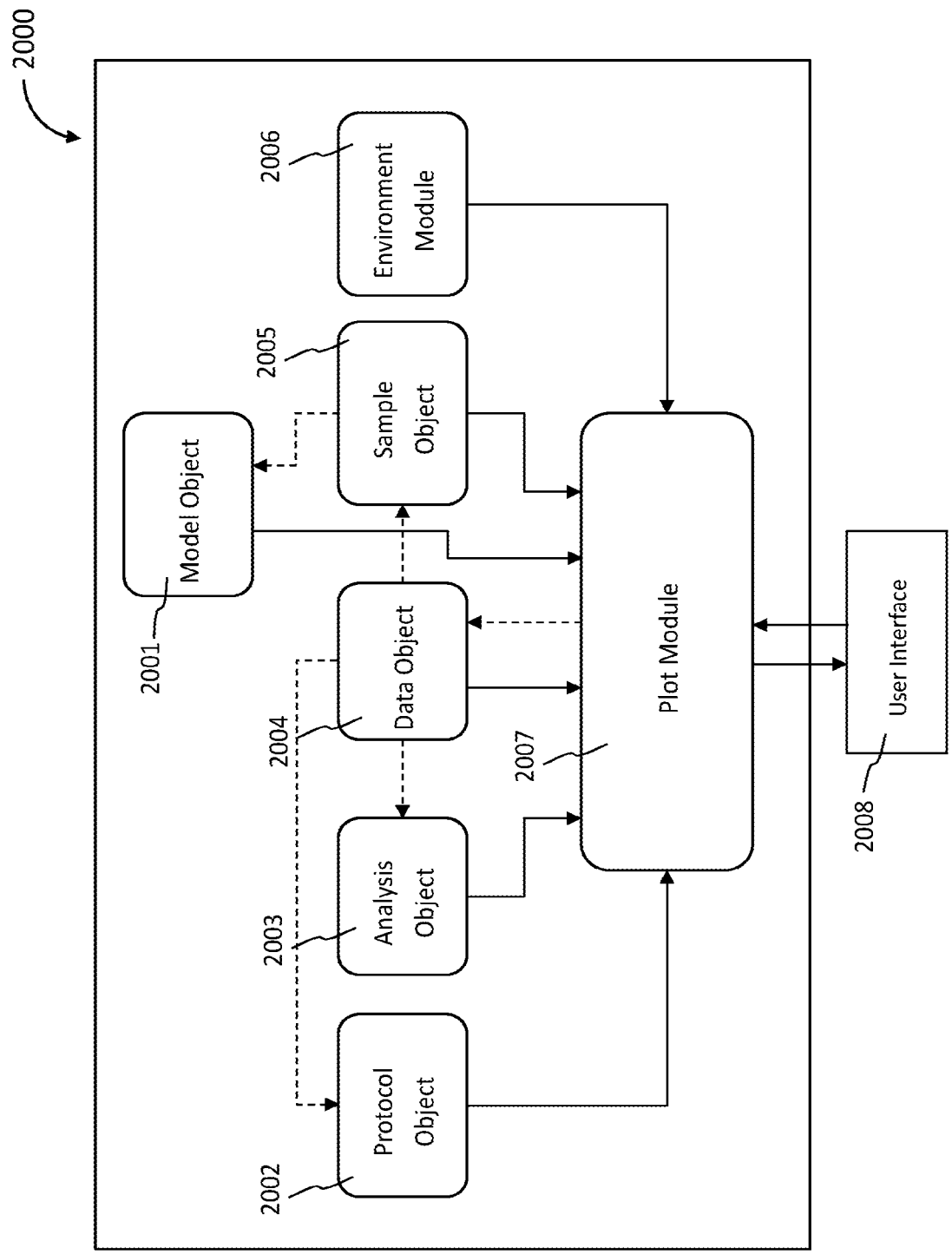
FIG. 20A-G illustrate a system of some embodiments of the present disclosure.
Figure 20B:
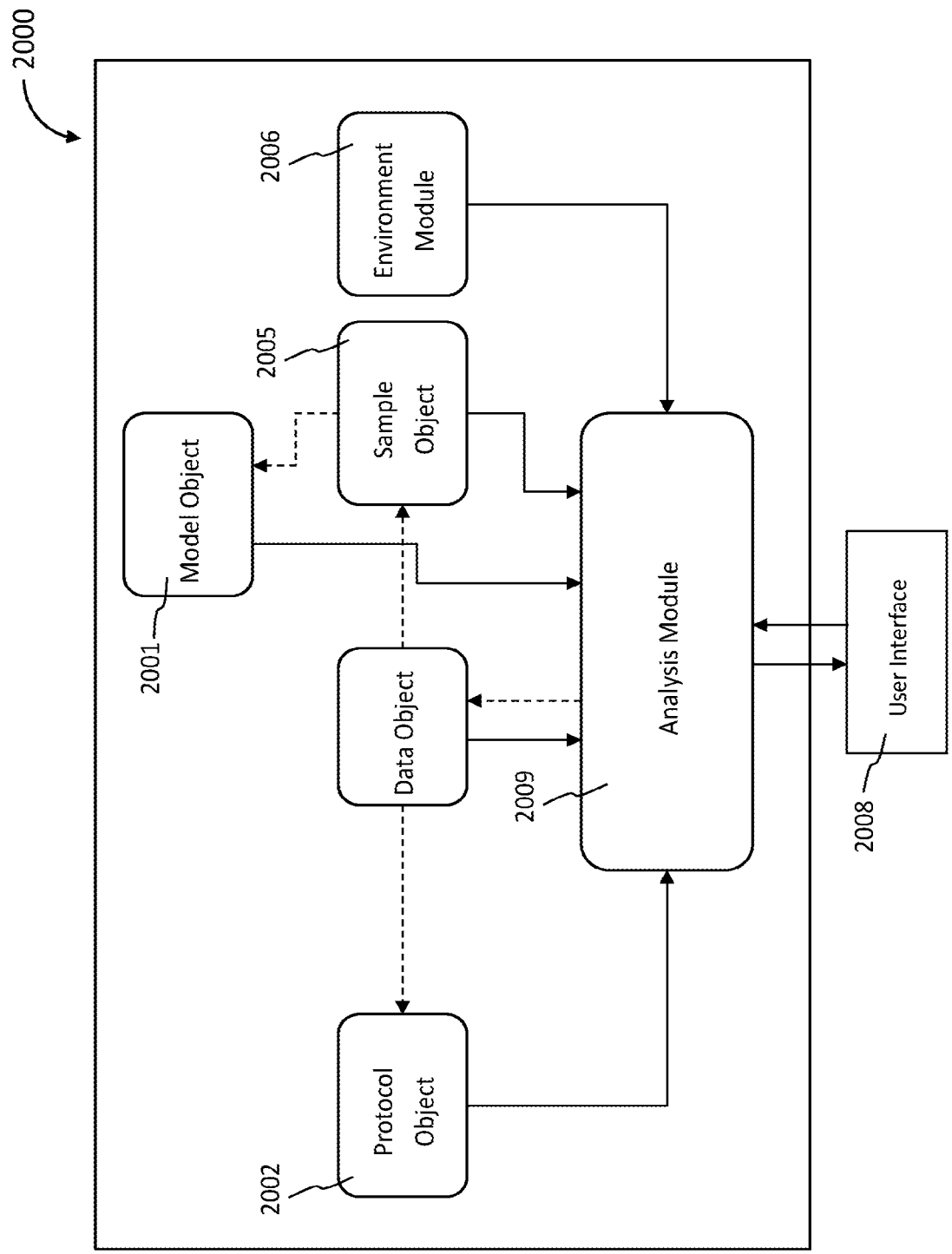
Figure 20C:
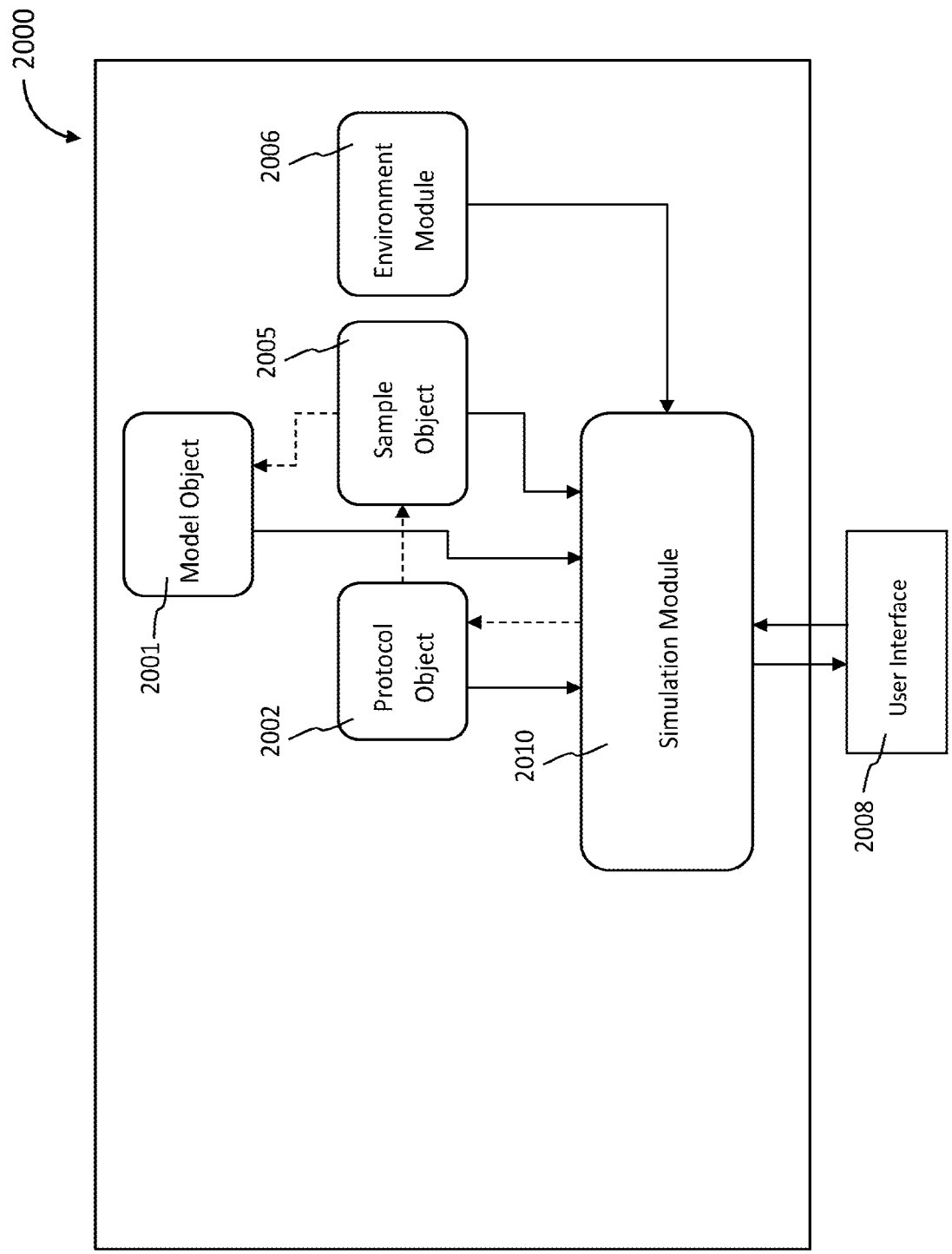
Figure 20D:
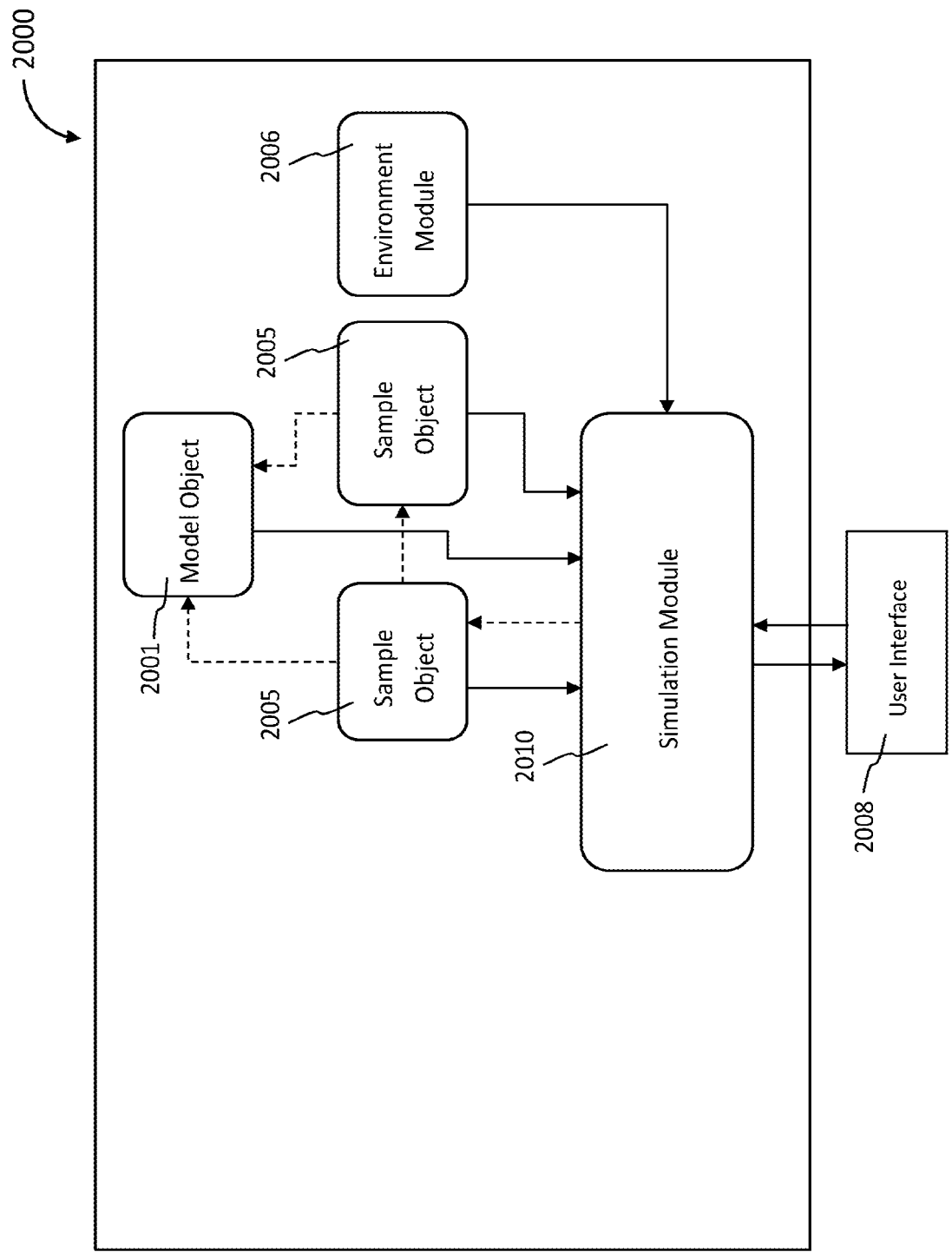
Figure 20E:
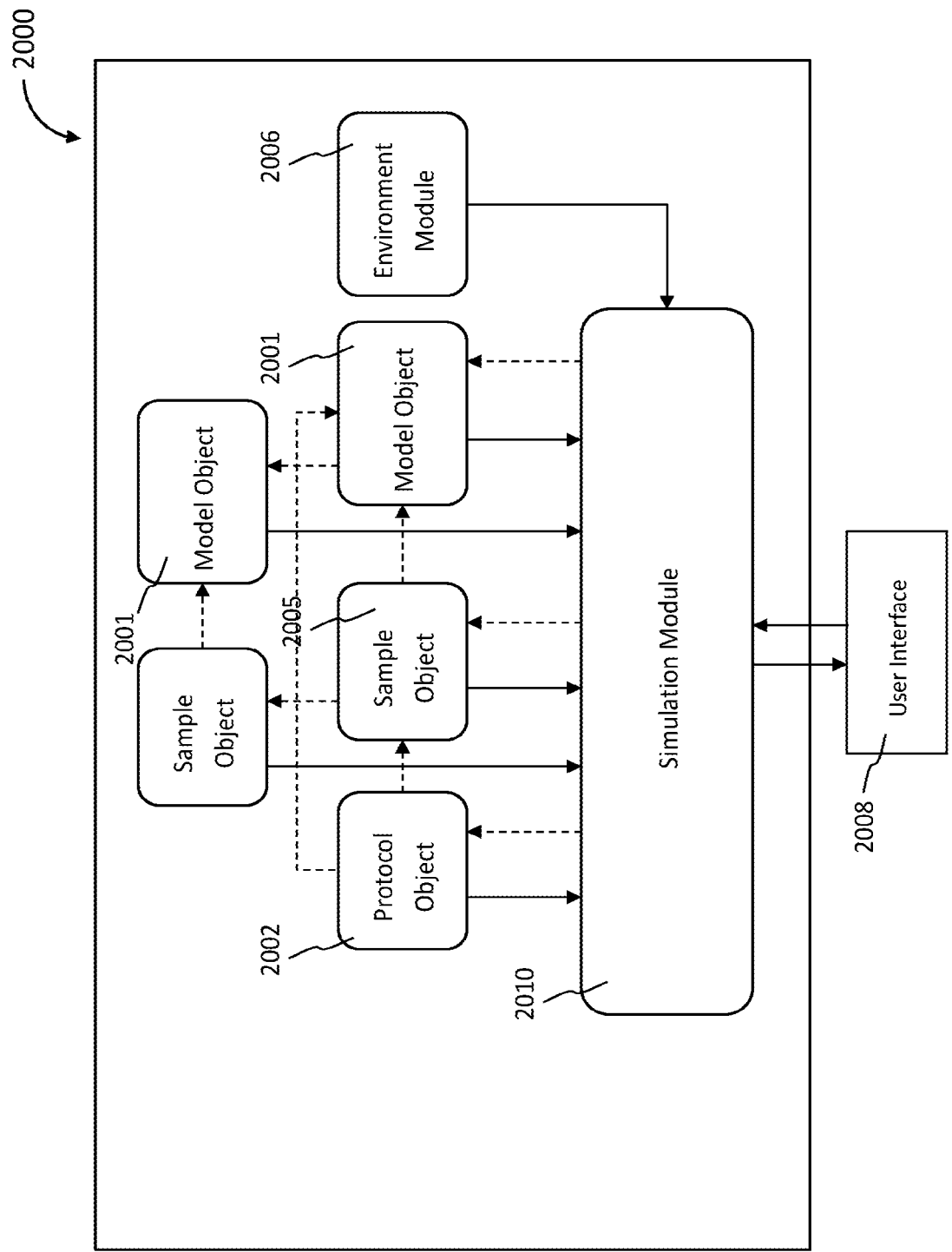
Figure 20F:
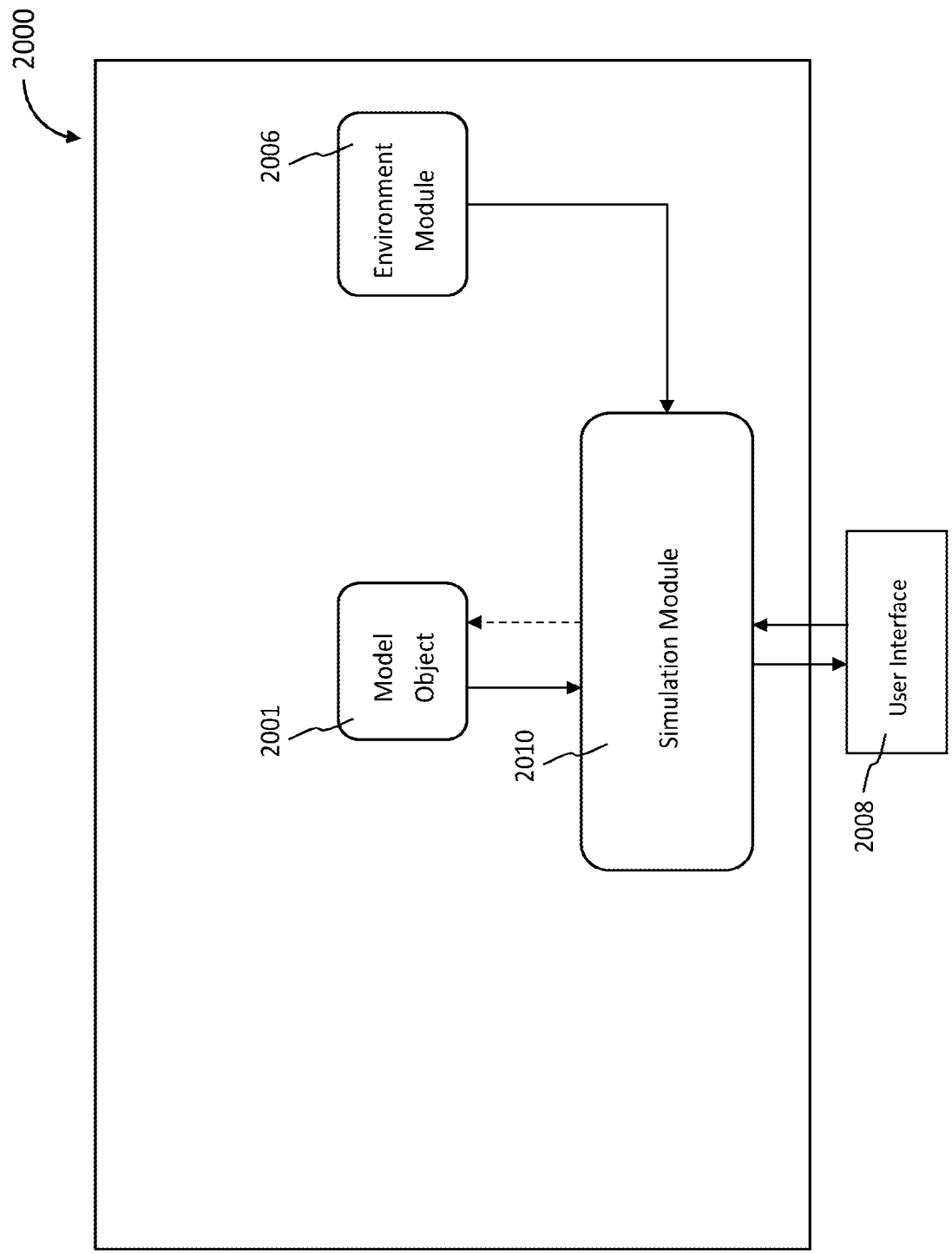
Figure 20G:
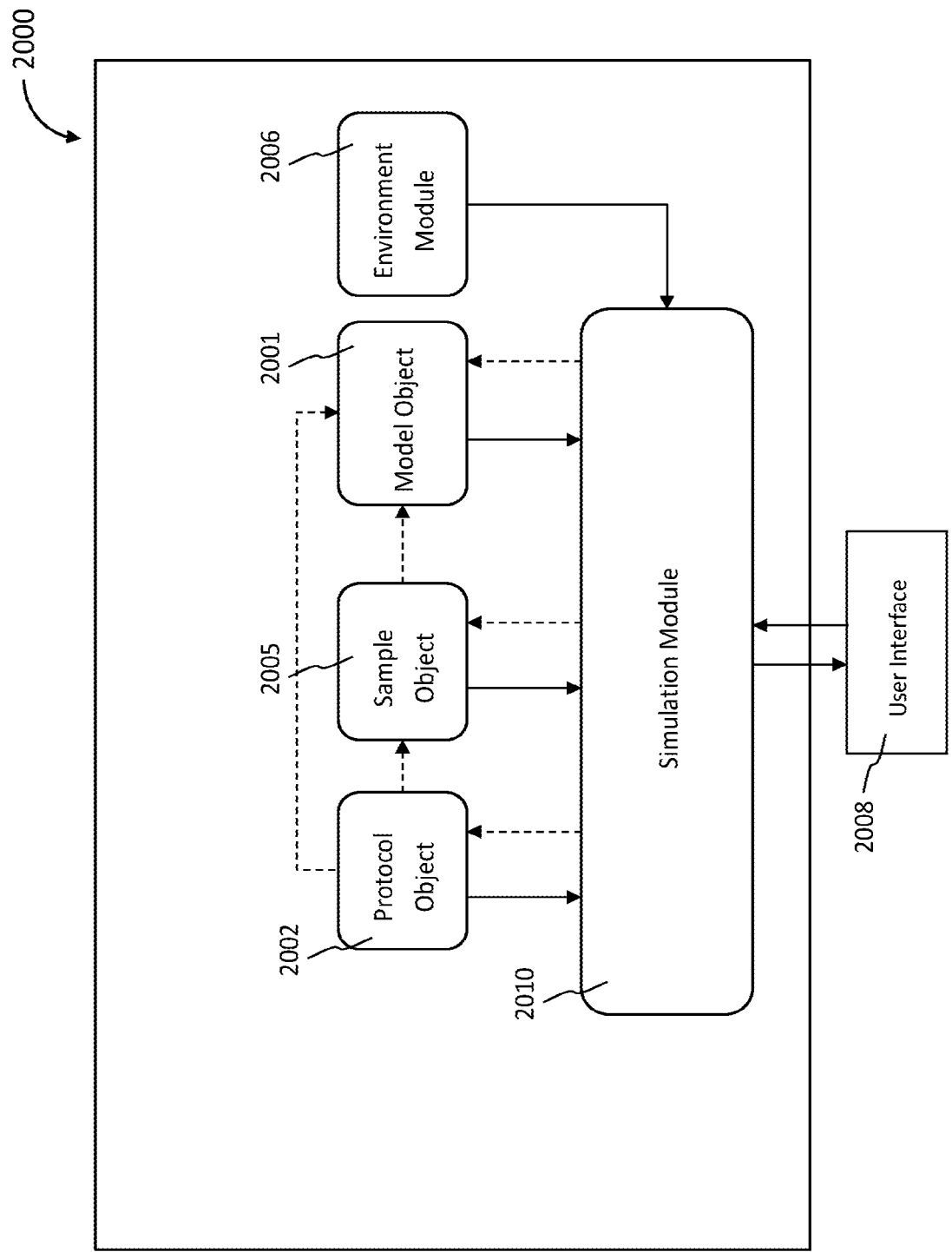

For example, in FIG. 20A the user activates the Plot Module (2008) and causes it to access a Data Object (2004) which contains the Data generated by a specific experiment. The Plot Module accesses the link in the Data Object to the Protocol Object (2002) to identify the Protocol Object and retrieve the information that it requires from the Protocol Object. It similarly accesses the links from the Data Object to the Analysis Object (2003) and Sample Object (2005) to identify and retrieve the information that it requires from those objects. It also accesses the link in the Sample Object to identify and retrieve the pertinent information it requires from the Model Object (2001). Separately, the Plot Module (2007) may receive information from the Environment Module (2006). The Plot Module returns information pertaining to the desired Plot to the User Interface (2008). In one embodiment instead of an Environment Module there is instead an Environment Object that is accessed via similar link mechanics.

FIG. 20B-G depict similar actions used during the execution of Analysis (2009) and Simulation Modules. In the preferred embodiment the Plot, Analysis, and Simulation Modules (2010) only access links as needed, e.g., if the Module already has sufficient information to resolve a parameter, it may optionally not access a potentially relevant link even if it is present in an object. One skilled in the art will readily appreciate that additional links to additional objects beyond those depicted here may be present and may be accessed by the Module as needed using the same set of actions as described herein. For example, in FIG. 21 the Data Object could potentially point to multiple Sample Objects which the Analysis Module could identify and retrieve information from.

Additionally, in some embodiments a Module may work together with another Module. For example, an Analysis Module may call a Plot Module to plot out the output of the Analysis Module.

In some embodiments, the system 2000 includes one or more experiment module configured to store values for experimental parameters for executing an experiment. Each experiment module can represent an experiment (or experiment technique) so that multiple experiments modules can represent multiple experiments, which may be interrelated. Alternatively, an experiment module may represent more than one experiments.

In addition, a data module can be included in the system and is configured to store results from the experiment. In some embodiments, the data stored in the data module can also be retrieved or used by the experiment module. In one embodiment, the system further includes an instrument module that is configured to store information about the instrument on which the experiment was run. An experiment may use more instruments which can be represented by one or more instrument modules.

Yet in another embodiment, the system includes an environment module configured to store environmental conditions under which the experiment was run. Examples of environmental conditions are described above.

Without limitation, the system can also include a data analysis, exploration or visualization module. The data analysis, exploration or visualization module is configured for analyzing and/or visualizing data of the experiment. In one embodiment, the analysis or visualization is based on results stored in the data module, but can further include one or more reference data point, or the representation thereof, from other data sources. Examples of such data sources are the experiment module, the data module, the instrument module, or the environment module. For data visualization, the reference data point can be displayed on a user interface, along with the results from the experiment.

In some embodiments, the reference data point is a result from a second experiment that is related to the experiment being analyzed. In some embodiments, the relationship is that reference data point imposes a limitation on interpretation of the results. For instance, the reference data point helps eliminate a portion of the results as not relevant to analysis of the data, validates or invalidate the results, or serves as standard or control to the results.

The present disclosure, in another embodiment, provides a system for analyzing data obtained from a laboratory experiment, comprising a processor, memory, and program code comprising an experiment module configured to display identification of a sample used in an experiment, identification of an instrument for carrying out the experiment, identification of a data set generated from the experiment, and identification of an environmental record that comprises measurement of environmental conditions when and where the experiment was conducted, a data module configured to display data extract or visualization to represent a data set, identification of an experiment that generated the data set, and identification of an analysis performed on the data set; an instrument module configured to display a listing of experiments carried out on an instrument, a listing of control experiments run on the instrument, and a maintenance record for the instrument; an analysis module configured to display identification of a data set for which an analysis was made, and an analysis summary or figure that represents a result of the analysis; and an environment module configured to display environmental conditions when and where an experiment was conducted, wherein the system enables a user to explore information pertaining to an experiment while the user is presented with an experiment panel displayed by the experiment module, by: (1) allowing the user to click on the identification of a data set generated from the experiment on the experiment panel, and thereby invoking the data module to display identification of an analysis performed on the data set on a data panel, which allows the user to click on the identification of analysis performed on the data set to invoke the analysis module to display an analysis summary or figure that represents a result of the analysis on an analysis panel; (2) allowing the user to click on the identification of an environmental record and thereby invoking the environment module to display environmental conditions when and where the experiment was conducted; and (3) allowing the user to click on the identification of an instrument for carrying out the experiment and thereby invoking the instrument module to display, on an instrument panel, a listing of control experiments run on the instrument, and a maintenance record for the instrument relevant to the experiment.

In some embodiments, the program code further comprises a sample module configured to display the identifications of a first experiment from which the sample is generated and a second experiment that is performed on the sample.

In some embodiments, the displayed analysis summary or figure on the analysis panel allows the user to make adjustment and access to the data set from which the analysis summary or figure is generated.

In some embodiments, the system allows the user to click on the listing of experiments on the instrument panel to view one or more other experiments conducted on the instrument for comparison.

Although the discussions above may refer to a specific order and composition of method steps, it is understood that the order of these steps may differ from what is described. For example, two or more steps may be performed concurrently or with partial concurrence. Also, some steps that are performed as discrete steps may be combined, steps being performed concurrently or in tandem may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention. Such variations will depend on the software and hardware systems chosen and on designer choice. It is understood that all such variations are within the scope of the invention. Likewise, software and web implementations of the present invention could be accomplished with standard programming techniques and logic to accomplish the various database searching steps, correlation steps, comparison steps and decision steps.

Unless otherwise defined, all technical and scientific terms used herein have the same meaning as what is commonly understood by one of ordinary skill in the art to which this invention belongs.

The inventions illustratively described herein may suitably be practiced in the absence of any element or elements, limitation or limitations, not specifically disclosed here. For example, the terms "comprising", "including," "containing," etc. shall be read expansively and without limitation. Additionally, the terms and expressions employed here have been used as terms of description and not of limitation; hence, the use of such terms and expressions does not evidence an intention to exclude any equivalents of the features shown and described or of portions thereof. Rather, it is recognized that various modifications are possible within the scope of the invention claimed.

By the same token, while the present invention has been specifically disclosed by preferred embodiments and optional features, the knowledgeable reader will apprehend modification, improvement and variation of the subject matter embodied here. These modifications, improvements and variations are considered within the scope of the invention.

The invention has been described broadly and generically here. Each of the narrower species and subgeneric groupings falling within the generic disclosure also form part of the invention. This includes the generic description of the invention with a proviso or negative limitation removing any subject matter from the genus, regardless of whether or not the excised material is described specifically.

Where features or aspects of the invention are described by reference to a Markush group, the invention also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the invention has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A system for analyzing data obtained from an experiment, comprising a processor, memory, and program code that comprises:
one or more modules configured to:
store contextual information represented as linked objects, the contextual information comprising:
values for experimental parameters for executing the experiment;
results from the experiment;
information about an instrument on which the experiment was run;
environmental conditions under which the experiment was run;
information about a sample on which the experiment was run; and
an experiment protocol comprising instructions to run the experiment;
estimate an expected result based on the experimental parameters;
programmatically link at least a portion of the contextual information with a protocol object or protocol information;
process the protocol object or the protocol information to carry out the experiment to generate the results;
determine, based on the contextual information, a type of an initial visual representation that depicts the results from the experiment;
extract, from the linked objects, a subset of the contextual information;
determine, based on the subset of the contextual information:
a scale for the initial visual representation,
an upper limit or a lower limit of an axis of the initial visual representation, wherein any of the results outside the upper limit or the lower limit are hidden from the initial visual representation, and
one or more other attributes of the initial visual representation; and
dynamically generate the initial visual representation based upon the type, the scale and the upper limit or the lower limit, the one or more other attributes, and the expected result.

2. The system of claim 1, wherein the experiment comprises a first experiment, and the generation of the visual representation is further based on a reference data point that comprises a result from a second experiment.

3. The system of claim 1, wherein the generation of the visual representation is further based on a reference data point that imposes a limitation on interpretation of the results.

4. The system of claim 3, wherein the reference data point eliminates a portion of the results as not relevant to analysis of the data.

5. The system of claim 3, wherein the reference data point validates or invalidate the results.

6. The system of claim 3, wherein the reference data point serves as standard or control to the results.

7. The system of claim 1, wherein one of the experimental parameters specifies an operation of preparation or calibration of the instrument.

* * * * *